United States Patent
Soliz

(10) Patent No.: US 11,585,798 B1
(45) Date of Patent: Feb. 21, 2023

(54) DIELECTRIC MATERIALS FOR SENSING AND DETECTION OF TOXIC CHEMICALS

(71) Applicant: U.S. Army Combat Capabilities Development Command, Chemical Biological Center, Apg, MD (US)

(72) Inventor: Jennifer R Soliz, Baltimore, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 749 days.

(21) Appl. No.: 16/269,988

(22) Filed: Feb. 7, 2019

Related U.S. Application Data

(60) Provisional application No. 62/635,809, filed on Feb. 27, 2018.

(51) Int. Cl.
*G01N 33/00* (2006.01)
*C01G 23/00* (2006.01)
*C01G 25/02* (2006.01)

(52) U.S. Cl.
CPC ....... *G01N 33/0057* (2013.01); *C01G 23/006* (2013.01); *C01G 25/02* (2013.01); *C01P 2002/34* (2013.01); *C01P 2002/72* (2013.01); *C01P 2002/82* (2013.01); *C01P 2002/88* (2013.01); *C01P 2006/40* (2013.01)

(58) Field of Classification Search
None
See application file for complete search history.

(56) References Cited

U.S. PATENT DOCUMENTS

| | | | | |
|---|---|---|---|---|
| 4,505,803 A | * | 3/1985 | Mase | G01N 27/122 219/505 |
| 5,071,770 A | * | 12/1991 | Kolesar, Jr. | G01N 27/4141 436/151 |
| 6,720,710 B1 | * | 4/2004 | Wenzel | F04B 43/046 417/474 |
| 6,821,738 B2 | * | 11/2004 | Harmon | G01N 21/31 435/7.1 |
| 2013/0144131 A1 | * | 6/2013 | Wang | A61B 5/021 600/301 |

FOREIGN PATENT DOCUMENTS

DE 102014226810 A1 * 6/2016 ........... G01N 33/004

OTHER PUBLICATIONS

Agarwal et al., One-Step Synthesis of Hollow Titanate (Sr/Ba) Ceramic Fibers for Detoxification of Nerve Agents, 2012, Hindawai Publishing Corporation, Journal of Nanotechnology, v. 2012, Article ID 429021, p. 1-7. (Year: 2012).*
Translation of DE 10 2014 226 810 A1, Fix et al. (Year: 2016).*

* cited by examiner

*Primary Examiner* — Lore R Jarrett
(74) *Attorney, Agent, or Firm* — Ulysses John Biffoni

(57) ABSTRACT

The invention is directed towards dielectric materials, $BaTiO_3$, $BaZrO_3$, and/or $BaTi_{1-x}Zr_xO_3$, such that $0 \leq x \leq 1$, for detecting, sensing, filtering, reacting, or absorbing toxic chemicals, such as chemical warfare agents ("CWAs") and their structural analogs, toxic industrial chemicals and narcotics, wherein the dielectric material is incorporated into a sensor for detecting, sensing, filtering, reacting, or absorbing the toxic chemicals.

5 Claims, 23 Drawing Sheets

DIELECTRIC MATERIALS FOR SENSING AND DETECTION OF TOXIC CHEMICALS

CROSS-REFERENCE TO RELATED APPLICATIONS AND CLAIM TO PRIORITY

This application claims the priority of U.S. Provisional Patent Application No. 621635,809, filed Feb. 28, 2018, which is incorporated herein by reference.

GOVERNMENT INTEREST

The invention described herein may be manufactured, used and licensed by or for the United States Government.

FIELD OF THE INVENTION

The invention relates to dielectric materials, specifically ferroelectric metal oxides such as compounds that contain barium, titanium, and zirconium, for detecting, sensing, filtering, reacting, or absorbing toxic chemicals, such as chemical warfare agents ("CWAs") and their structural analogs.

BACKGROUND OF THE INVENTION

Perovskites are materials that have physical properties including superconductivity, piezoelectricity, ferroelectricity, ferromagnetism, and magnetoresistance. The general formula of a perovskite is $ABX_3$, wherein the A-site cations are composed of low valent, large cations. Typically, transition metals occupy the B-sites and are usually high valent, small cations. These cations are surrounded by X-site anions, which is usually oxygen. For a simple cubic perovskite structure with the space group of Pm-3m (FIG. 1) the A-site is twelve coordinate while the B-site has an octahedral environment and is six coordinate. The nomenclature for a simple cubic perovskite is $ABX_3$ due to symmetry. One of the more commonly known simple cubic perovskites is $SrTiO_3$.

When an external electric field is reversed, the spontaneous electrical polarization within ferroelectrics will switch in hysteresis, and yet the polarization is maintained when the field is removed. Two common conditions imperative for such ferroelectricity to occur in perovskites is (1) the B-site must be a non-dielectric $d^0$ cation and (2) the symmetry must be a polar space group, so that the local electric dipoles do not cancel each other out. The electron counts in condition 1 are what facilitate a second order Jahn Teller ("SOJT") distortion. This structural distortion allows the mixing of the highest occupied molecular orbitals ("HOMO") with the lowest unoccupied molecular orbitals ("LUMO") since the band gap is small. The mixing of the HOMO and LUMO is symmetry forbidden, but if the B-site cation displaces out of the center of the octahedron (see FIGS. 2A and 2B), mixing of these orbitals is now permitted; thus, the HOMO and LUMO become stabilized and destabilized, respectively. The symmetry is then lowered, and an asymmetric coordination environment is generated due to the small atomic displacements producing the electrical dipole moment in the crystal.

One of the well-known perovskites that exhibits ferroelectricity is barium titanate ("$BaTiO_3$"; BTO). Its structural distortion allows for the mixing of the HOMO and LUMO, inducing an electrical polarization. Ferroelectrics are able to maintain polarization when the field is removed; hence remnant polarization ($P_r$) (see FIG. 3). The intra-octahedral distortion is the driving force for a variety of technologically advanced materials, such as ferroelectrics, capacitors, transducers, and non-linear optics, actuators, ferroelectric random-access memory ("FRAM"), and micro electro-mechanical systems ("MEMS").

Metal oxides are well known for detoxifying toxic chemicals, whereas metal oxides encompassing the perovskite crystal structure is not.

Agarwal et al. teaches $SrTiO_3$ and $BaTiO_3$ as detoxifying compound for VX and dimethyl chiorophosphite ("DMCP") in "One-Step Synthesis of Hollow Titanate (Sr/Ba) Ceramic Fibers for Detoxification of Nerve Agents" in Journal of Nanotechnology Volume 2012, Article ID 429021.

Kapoor et al. discloses mixed metal oxides used in many applications in the electronic industry as passive or active components in devices. These oxides exhibit high dielectric, and ferro- or pyroelectric properties, e.g., $BaTiO_3$, $LiNbO_3$, $KTaO_3$, $Pb_{1-x}La_xTi_yZr_2O_3$, etc. These MMO nanoparticles are used in anti-chemical and biological warfare, in air purification, and as an alternative to incineration of toxic substances, in "Mixed Metal Oxide Nanoparticles," Dekker Encyclopedia of Nanoscience and Nanotechnology (2004), Page 2007-2015.

Wagner et al. discloses hydrolysis of VX, GD, and HD on $Al_2O_3$, $TiO_2$ (anatase and rutile), and titanium metal powders in "27Al, 47, 49Ti, 31P, and 13C MAS NMR Study of VX, GD, and HD Reactions with Nanosize $Al_2O_3$, Conventional $Al_2O_3$ and $TiO_2$, and Aluminum and Titanium Metal, J. Phys. Chem. C (2007), Vol 111, pages 17564-17569.

Panayotov et al. discloses the thermal decomposition of dimethyl methylphosphonate ("DMMP"), a chemical warfare agent simulant, on high surface area $TiO_2$ nanoparticles (Degussa P25) in "Thermal Decomposition of a Chemical Warfare Agent Stimulant (DMMP) on TiO2: Adsorbate Reactions with Lattice Oxygen as Studied by Infrared Spectroscopy," J. Phys. Chem. C, 2009, Vol. 133, Issue 35, pages 14684-15691.

Park et al. discloses decomposition of CNCl in a $BaTiO_3$-filled Packed Bed Plasma Reactor in "Decomposition of Cyanogen Chloride by Using a Packed Bed Plasma Reactor at Dry and Wet Air in Atmospheric Pressure," Plasma Chemistry and Plasma Processing (2004), Vol. 24, Issue 1, pages 117-136.

WO2008058518 to Eickhoff et al. teaches a substrate having a hydrogen or to use hydrogenated surfaces as warfare agent detection devices.

WO200688477 to Rothschild et al. teaches using $SrTiO_3$, $BaTiO_3$, and $CaTiO_3$ substrates for sensing CWAs in gas.

WO200442366 to Houser et al. teaches barium titanate or zirconium titanate as piezoelectric sensors, useful for detecting toxic compounds.

JP2011078902 to Hirakawa et al. teaches decontamination agents such as $SrTiO_3$ and $BaTiO_3$. However, $SrTiO_3$ and $BaTiO_3$ have low decontamination rate for some chemicals such as 2-Chloroethyl ethyl sulfide ("2-CEES").

Therefore, there remains a need for other perovskites to detoxify these chemical warfare agents.

SUMMARY OF THE INVENTION

The present invention is directed towards at least one material for detecting, sensing, filtering, reacting, or absorbing toxic chemicals, such as chemical warfare agents (CWAs), the material is selected from the group consisting of $BaTiO_3$, $BaZrO_3$, $BaTi_{1-x}Zr_xO_3$, and mixtures thereof, wherein $0<x<1$, preferably x is 0, 0.01, 0.05, 0.1, 0.2, 0.25, 0.3, 0.4, 0.5, 0.6, 0.7, 0.75, 0.8, 0.9, 0.95, and 1.

Another aspect of the invention provides a sensor for detecting, sensing, filtering, reacting, or absorbing toxic chemicals, such as CWAs. The sensor contains at least a substrate and a sensing layer deposited on at least one surface of the substrate, wherein the testing layer contains $BaZrO_3$, $BaTiO_3$, and/or $BaTi_{1-x}ZrxO_3$. In certain embodiments, the sensor is constructed as a capacitor.

A further aspect of the invention provides a method for detecting, sensing, filtering, reacting, or absorbing toxic chemicals. The method contains the step of contacting the sensor or the material containing $BaTiO_3$, $BaZrO_3$, and/or $BaTi_{1-x}Zr_xO_3$ with a sample, and determining the change in properties of the material or the sensing layer of the sensor.

Other aspects of the invention, including kits, formulations, intermediates, and the like which constitute part of the invention, will become more apparent upon reading the following detailed description of the exemplary embodiments.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. The objects and advantages of the invention will become apparent from a study of the following specification when viewed in light of the accompanying drawings, in which like elements are given the same or analogous reference numerals and wherein.

DETAILED DESCRIPTION OF THE PREFERRED EMBODIMENT(S)

The present invention is directed towards dielectric materials that contain barium, titanium, and/or zirconium that react and decontaminate toxic chemicals, such as chemical warfare agents ("CWAs"), industrial hazards, narcotics, and their simulants. The reaction is correlated to a change in the net electric dipole moment from the dielectric materials. Useful dielectric materials include, but are not limited to, $BaTiO_3$, $BaZrO_3$, and $BaTi_{1-x}Zr_xO_3$, wherein 0<x<1. Preferably, x is 0, 0.01, 0.05, 0.1, 0.2, 0.25, 0.3, 0.4, 0.5, 0.6, 0.7, 0.75, 0.8, 0.9, 0.95, and 1.

The CWA may be in the forms of gas or liquid. The CWAs include, but are not limited to, nerve agents including tabun, sarin, soman, cyclosarin, pinacolyl methylphosphonofluoridate, cyclohexyl methylphosphonofiuoridate, methylphosphonothioic acid S-(2-(bis(I-methylethyl)amino)

ethyl) O-ethyl ester), O-ethyl S-(2-diisopropylamino)ethyl methylphosphonothioate (VX), phosphonofluoridic acid, ethyl-, isopropyl ester), phosphonothioic acid, ethyl-, S-(2-(diethylamino)ethyl) O-ethyl ester), Amiton, phosphonothioic acid, methyl-, S-(2-(diethylamino)ethyl) O-ethyl ester) blister/vesicant agents, e.g., lewisite, mustard-Lewisite, nitrogen mustards (HN-1, HN-2, HN-3), phosgene oxime, sulfur mustards (H, HD, HT); cyanogen chloride, hydrogen cyanide, chlorine, chloropicrin, diphosgene, phosgene, other toxic organophosphorus-type agents, their analogs or derivatives, and other similar art-known toxins, and the like. A chemical precursor includes gases or vapors known in the art to be used in the preparation of chemical warfare agents. A decomposition product includes gases or liquids known in the art to result from reaction or decomposition of a chemical warfare agent with oxygen, water, sunlight, biological tissue, and the like. Preferred CWAs include sulfur mustard and sarin.

The industrial hazards may be gas or liquid and include, but are not limited to, hydrogen cyanide, chlorine, chloropicrin, diphosgene, sulfur dioxide, hydrogen sulfide, and hydrogen fluoride. The narcotics include, but are not limited to, fentanyl, remifentanil, carfentanil, or other opioids.

$BaTiO_3$, $BaZrO_3$, and $BaTi_{1-x}Zr_xO_3$ undergo changes to its properties when exposed to toxic chemicals, such as CWA and their simulants. The changes are detectable in ferroelectric spectrum, impedance spectrum, Raman spectrum, infrared (IR) spectrum, ultra-violet visible (UV-Vis) spectrum, X-ray photoelectron spectrum, ultra-violet photoelectron spectrum, electron microscopy diffraction as well as images, thermogravimetric analysis spectrum, surface plasmon spectrum, nuclear magnetic resonance spectrum, or combinations thereof. For example, the impedance of $BaTiO_3$ at room temperature decreased by 5 orders of magnitude when exposed to DMCP, e.g., as shown in FIG. 8.

$BaTiO_3$ may be made by conventional solid-state synthesis. Specifically, $BaCO_3$ and $TiO_2$ powders were ground for about 30 min in an agate mortar and pestle. The powder was then calcined, e.g., at about 1100° C. with a ramp rate of 10° C/min and a dwell of 16 h in air. The same method may also be used to synthesize $BaTi_{1-x}Zr_xO_3$ with the addition of $ZrO_2$ as the starting reagent.

$BaTi_{1-x}Zr_xO_3$ may also be prepared, e.g., by a mixed oxide method. In this method, $BaCO_2$, $ZrO_2$, and $TiO_2$ were homogenized and ball milled in a solvent, such as isopropyl alcohol, to form a powder. The powder was then dried and compacted to form pellets. The pellets were then sintered, e.g., at about 1550° C. for about 4 hours in static air, and then cooled to room temperature to form $BaTi_{1-x}Zr_xO_3$.

$BaZrO_3$ may be synthesized by grinding $BaCO_3$ and $Zr(OH)_4$ powders in a solvent, e.g. methanol. The powder was then dried, and subsequently calcined, e.g., in air at about 1100° C. overnight.

$BaZrO_3$, $BaTiO_3$, and $BaTi_{1-x}Zr_xO_3$ are environmentally friendly, non-toxic piezoelectric materials, and $BaTiO_3$ and $BaTi_{1-x}Zr_xO_3$ ($x \leq 0.1$) are non-toxic ferroelectric materials. These materials are useful for interacting with CWAs or simulants, resulting in a change in polarization. This change is thus an indication that the piezoelectric material has reacted with CWA(s), i.e. meaning CWAs are present, and therefore acts as a sensor as well. The piezoelectric or ferroelectric materials are applicable in a device for detecting, sensing, filtering, reacting, or absorbing toxic chemicals or used as a decontaminant wipe, or a sprayable slurry for decontamination or chemical removal. As a sensor, this could also be coupled with a fielded drone, wherein the sensor could provide information on detecting the type of CWA present in the field.

$BaZrO_3$, $BaTiO_3$, and $BaTi_{1-x}Zr_xO_3$ are also photoactive, and they are useful as photoelectrodes or applied toward photocatalysis. These materials are also semi-conductors, which have charge carrier transport applications. Exhibiting these properties could lead to other relevant applications for CWAs.

Useful amount of $BaZrO_3$, $BaTiO_3$, and $BaTi_{1-x}Zr_xO_3$ is about 10 mg of material to 1μL or lesser amounts of chemical warfare agents or other chemicals. FIG. 18 shows the percent conversion of DMMP, DMCP, and 2CEES (1μL initial volume) after contact with $SrTiO_3$, $BaZrO_3$, and $BaTiO_3$ for one hour.

The chemistry of CWAs with different materials can vary; however, the major reaction of interests to these technologies is nucleophilic attack. Specifically, the nucleophilic attack with CWAs is the cause for molecular dissociation of the CWAs; thereby causing decontamination. See FIGS. 11A and 11B for the mechanism of the reaction. Similar reactions also occur with simulants of CWAs.

In the form of a sensor, $BaZrO_3$, $BaTiO_3$, and/or $BaTi_{1-x}Zr_xO_3$ may be deposited on to a substrate as at least one layer. These materials may be incorporated with a polymer or solution to form a composite mixture. As shown in FIG. 5, a sensor 100 contains at least two layers: a substrate 102 and a sensing layer 104 containing $BaZrO_3$, $BaTiO_3$, and/or $BaTi_{1-x}Zr_xO_3$. Substrate 102 may be a textile material, crystalline or amorphous structural support, a polymer, a dielectric, paper, a film, a fabric, a foam, or combinations thereof. Substrate 102 may also be an interdigitated capacitor or interdigitated electrode. Although FIG. 5 shows sensing layer 104 deposited onto a single surface of substrate 102, sensing layer 104 may be deposited onto one or more surfaces of substrate 102. Sensing layer 104 contains one or more coatings of $BaZrO_3$, $BaTiO_3$, and/or $BaTi_{1-x}Zr_xO_3$ or composite thereof.

For detection, sensor 100 contacts a sample suspected of containing a toxic chemical, such as CWA. Sensing layer 104 of sensor 100 is then analyzed for changes in its properties, such as, but not limited to, ferroelectric spectrum, impedance spectrum, Raman spectrum, infrared (IR) spectrum, ultra-violet visible (UV-Vis) spectrum, X-ray photoelectron spectrum, ultra-violet photoelectron spectrum, electron microscopy diffraction as well as images, thermogravimetric analysis spectrum, surface plasmon spectrum, nuclear magnetic resonance spectrum, or combinations thereof. Changes in one or more of these properties indicates the presence of the toxic chemical in the sample. Preferably, the impedance of sensing layer 104 is measured, wherein a change in impedance of the sensing layer 104 indicates the presence of the toxic chemical. A "finger print" spectrum may be determined for the toxic chemical by comparing the results of standards containing the toxic chemical. The presence of the "finger print" pattern during the analysis indicates the presence of the toxic chemical in the sample. In certain embodiments, measurements of the changes are made only at characteristic frequencies where greatest changes occur when sensing layer 104 is exposed to the toxic chemical. At least a 5%, preferably at least a 30%, more preferably at least a 50%, most preferably at least a 100% change in impedance or a change in the phase angle is needed to confirm the presence of the toxic chemical at a frequency in the range of 1 MHz to 0.01 Hz.

In an embodiment, the sensor is formed of a parallel plate capacitor. As shown in FIG. 6, a parallel plate capacitor 200 contains a sensing layer 202 sandwiched between two capacitor plates 204 and 206. On exposure to a sample suspected of containing a toxic chemical, the impedance of parallel plate capacitor 200 may be measured by methods well-known in the art to indicate the presence of the toxic chemical.

Figure 7:
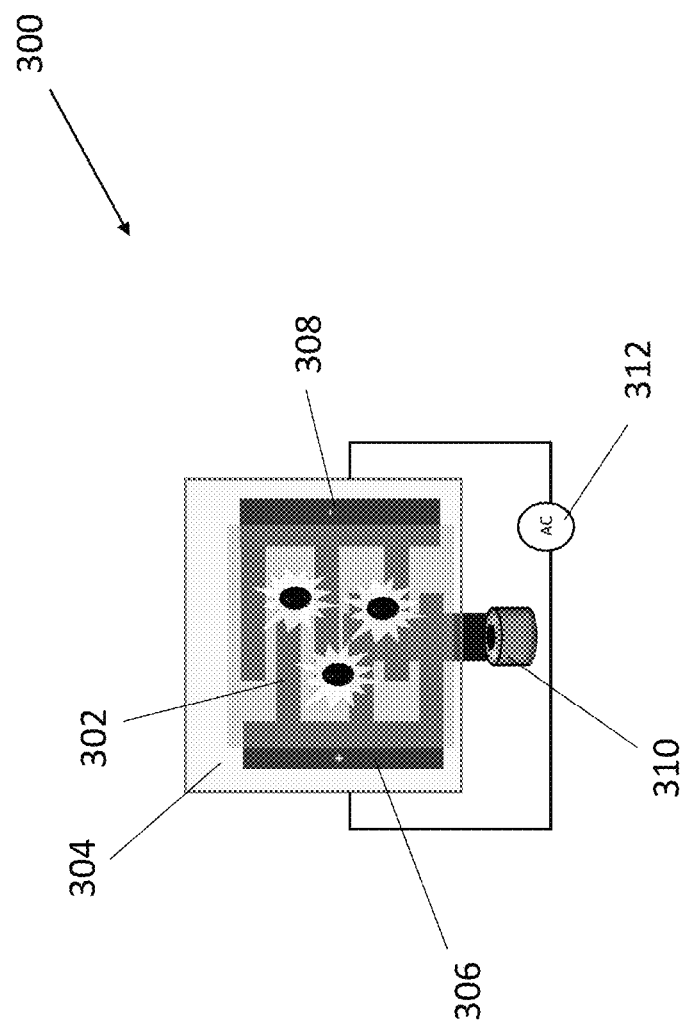
FIG. 7 depicts an interdigitated electrode of the present invention.

In another embodiment, as shown in FIG. 7, a sensor is formed of an interdigitated capacitor or interdigitated electrode. The interdigitated electrode 300 contains a sensing layer 302 coated on a substrate 304 with a positive electrode 306 and a negative electrode 308 in contact with sensing layer 302. On exposure to a sample suspected of containing a toxic chemical, the impedance of interdigitated electrode 300 or an optical measurement, e.g. Raman, infrared, and ultra-violet visible spectra, may be measured by methods well-known in the art to indicate the presence of the toxic chemical. For example, the impedance may be measured via a circuit 312; and the optical measurement may be measured via an optical source 310. Interdigitated electrode 300 may be designed as a circuit to include blue-tooth remote communication capability, a battery, and/or data storage.

EXAMPLE 1

Solid State Synthesis $BaTiO_3$ and $BaZrO_3$ exhibit ferroelectricity and piezoelectricity, respectively, and provide a basis for understanding the electronic and structural properties in $BaTi_{1-x}Zr_xO_3$ solid solutions. The $Ti^{4+}$ and $Zr^{4+}$ within in $BaTi_{1-x}Zr_xO_3$ led to piezoelectricity, ferroelectricity (found in some compositions) and absorption of CWA structural analogs. The change in bond lengths due to the net displacement of all the ions causes the electrical polarization in these crystal structures. Structural characterization of these materials was carried out by performing Rietveld refinements from gathered X-ray diffraction patterns. In-depth understandings of the crystal structure i.e. bond distances, bond angles, and lattice structure, confirmed identification of aforementioned compounds.

Electrical Characterization

Sintered pellets of the aforementioned oxides were prepared, and their electrical properties were measured using ferroelectric tester or impedance spectroscopy. Understanding the impact on their dielectric properties as well as the electrical polarization influenced from the reactivity with CWA structural analogs was crucial for changes in the charge transport. Furthermore, changes to the bond lengths owing to the net polarization were further studied by carrying out these measurements. When applying an external electric field, the applied electric field causes a shift in the ions; thus, resulting in polarization. Once the field is removed, the ferroelectric materials maintain their polarization. Since all the ions have been shifted, the movement of the cations with the electric field is important, as the movement affects the B-O bond distances. Thus, chemisorption of the CWA structural analogs to the surface of the metal oxide greatly influences the electronic properties.

Spectral Characterization

The adsorption and reaction of CWA structural analogs on perovskite films were characterized via an environmental infrared spectroscopy. Briefly, a substrate, such as a diamond crystal, was coated via spin-coating with a thin (about 1μm) film of interest ($BaTiO_3$, $BaZrO_3$, or $BaTi_{1-x}Zr_xO_3$). The crystal was then placed into a reactor cell that enabled the control of the environment (liquid or gas phase components and temperature). For gas-phase reactions, an ambient pressure sampling mass spectrometer was used downstream to analyze byproducts.

Figure 4:
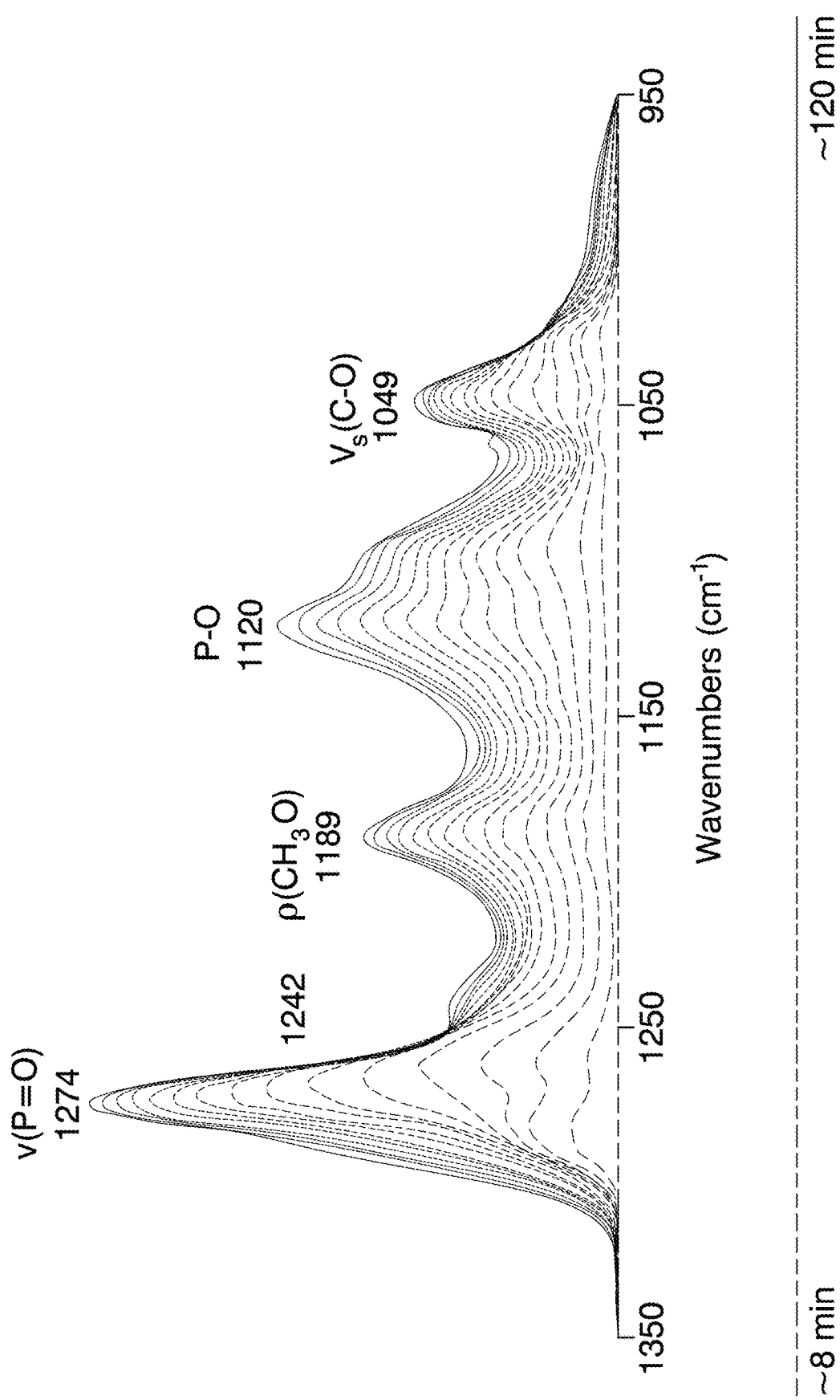
FIG. 4 depicts an in-situ infrared spectra, showing the molecular dissociation of a G-type agent as it interacts with $BaTiO_3$.
Figure 5:
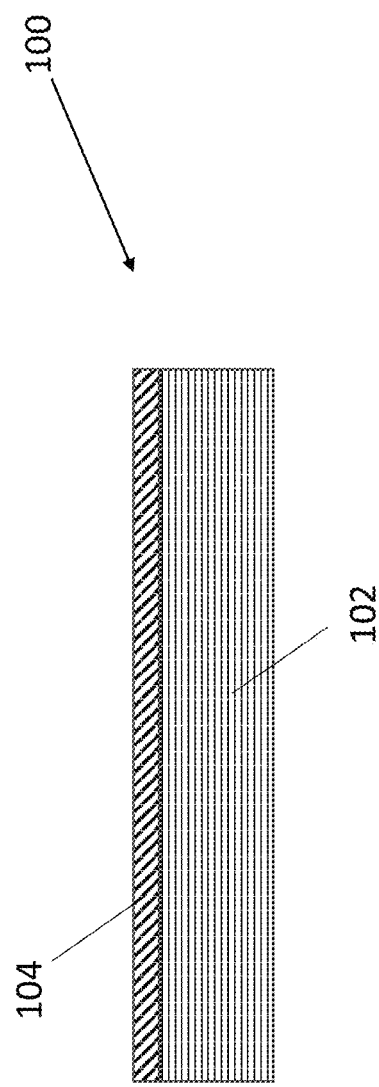
FIG. 5 depicts a sensor of the present invention.
Figure 6:
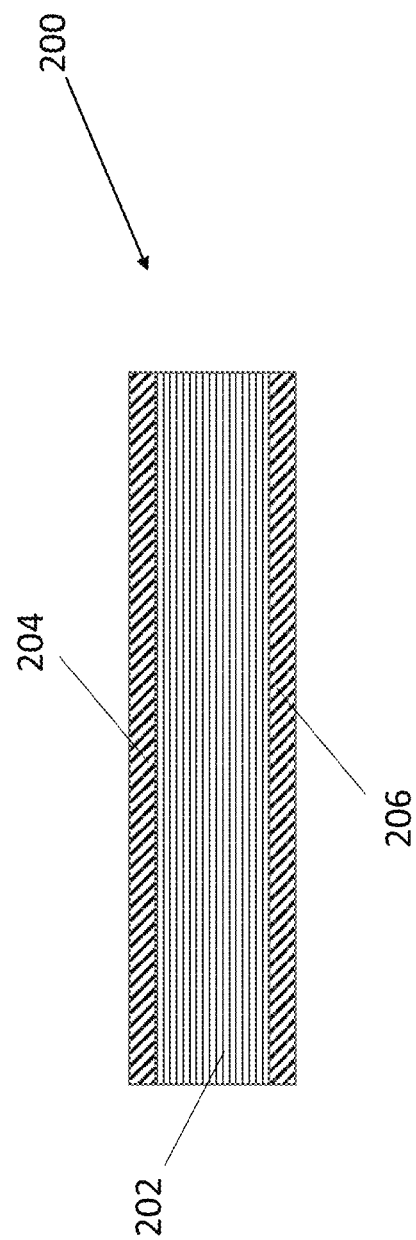
FIG. 6 depicts a parallel plate capacitor of the present invention.

Subsequently, an in-situ study with CWA structural analogs using DRIFTS was executed, to gain a mechanistic understanding of the molecular dissociation of the CWA structural analogs on the surface of the dielectric materials. Characteristic vibrational stretches from a given analyte provided insights about the mechanism. As shown in FIG. 4, the molecular dissociation of one of the G-type CWA simulants as it interacts with $BaTiO_3$. The presence of the phosphoryl oxygen (v(P=O) at about 1274 $cm^{-1}$) and v(P-31 O) at or near about 1120 $cm^{-1}$ provides evidence that molecular dissociation has occurred.

Figures 17A, 17B, 17C:
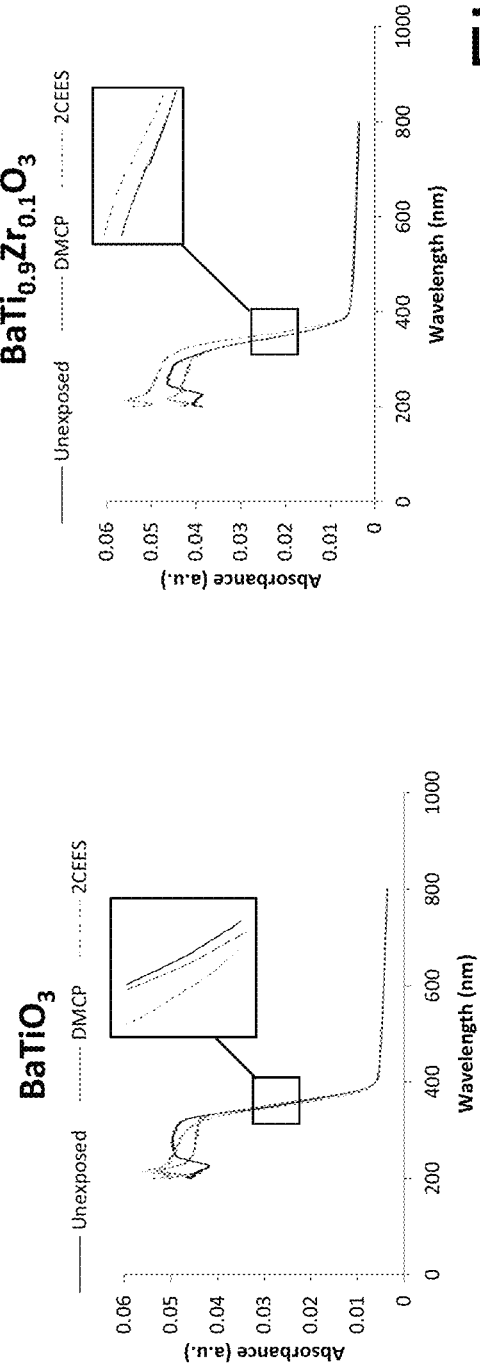
FIGS. 17A and 17B respectively depict the ultra-violet visible (UV-Vis) spectra of $BaTiO_3$ (FIG. 17A, black solid line) and $BaTi_{0.9}Zr_{0.1}O_3$ (FIG. 17B, black solid line) exposed to 10 weight % of DMCP (grey solid line) and 2-CEES (grey dashed line) for 1 minute.
FIG. 17C is a table showing the calculated band gap energies of $BaTiO_3$ and $BaTi_{0.9}Zr_{0.1}O_3$.

The ultra-violet visible (UV-Vis) spectra on unexposed and exposed $BaTiO_3$ and $BaTi_{0.9}Zr_{0.1}O_3$ was collected using a Jasco V-750 spectrophotometer equipped with a 60 mm integrating sphere. Each of the samples were exposed ex-situ to 10 weight % of DMCP and 2-CEES for 1 min. Prior to all measurements, a baseline was collected of the empty integrating sphere cell. There is a broad UV emission band peak centered at about 300 nm (FIGS. 17A and 17B), correlating to physisorbed water on the surface. This peak attenuates with the DMCP exposure, as expected from the loss of surface hydroxyls and change in structure morphology. The peak centers at about 200 nm (FIGS. 17A and 17B) from the exposed samples originated from excitonic recombination. The band gaps were determined, using a tangent line to the adsorption edge. The results are reported in FIG. 17C.

Methods $SrTiO_3$, $BaTiO_3$, $BaZrO_3$, and $BaTi_{1-x}Zr_xO_3$ perovskites or dielectric materials of the present invention were synthesized via the conventional solid-state synthesis method well known in the art. CWA structural analogs, such as sarin, DMMP, DMCP, and 2-CEES, were exposed to the perovskites. The results for newly synthesized perovskites $BaZrO_3$, $BaTi_{1-x}Zr_xO_3$, $SrTiO_3$, and $BaTiO_3$ were compared to the well-studied $TiO_2$, $ZrO_2$, and $Zr(OH)_4$ materials.

The aforementioned perovskites in the forms of sintered pellets or films were exposed to the given CWA structural analog inside a closed container, to determine the dosage of the perovskites. Specifically, within the closed container, the surface of the metal oxide or film reacts with the vapors stemming from the given CWA structural analog, and a range of concentrations (i.e. trace to low bulk levels) of the perovskites were explored.

In-situ DRIFTS results provided insights about the chemical interaction between the analyte and material of interest, i.e. molecular dissociation of the CWA structural analogs. Spectra were obtained in the reflection mode.

The permittivity of dielectric materials was measured with ex-situ and in-situ chemical exposure using a Solartron 1260 Impedance analyzer. The measurement of the impedance and the dielectric constant as a function of frequency provides parameters for simple circuit designs.

The perovskites thin films or the composite perovskites thin films were incorporated as at least one active layer in interdigitated capacitor ("IDC") heterostructures. The impedance of the perovskite component at 1 MHz and 1 Hz frequencies were analyzed to establish a selectivity via an impedance "fingerprint" for the analyte. The perovskite layer was integrated as a sub-layer film to an IDC, or as an overlay onto the IDC. Fabrication of the IDC structures were achieved using photo- and electron-beam lithography in conjunction with ultra-sonic spray deposition. By coupling the electronic and spectral properties exhibited within these IDC heterostructures two main capabilities were demonstrated: (1) catalytic breakdown capabilities of the perovskite layer, and (2) tuning the electrical and spectral properties of the IDC heterostructures used to detect the presence of a given analyte. Copper metal was incorporated as electrodes in the IDC design due to its low cost, high conductivity, high abundance, and adhesive compatibility with protective over-layers when necessary. The impedance results are shown in Table 1.

TABLE 1

Impedance - Percent Increase

|  | 1 MHz | | 1 Hz | |
| --- | --- | --- | --- | --- |
|  | 2-CEES | DMCP | 2-CEES | DMCP |
| $SrTiO_3$ | 15.6% | 34.4% | 13.6% | 36.9% |
| $BaTiO_3$ | 907000% | 855000% | 3470000% | 3420000% |
| $BaZrO_3$ | 22.9% | 18.9% | 25.8% | 20.1% |

Several potential uses for this material include: a process for (a) decontaminating or removing CWAs, specifically G, V, and H agents, (b) sensing the presence of CWAs, and (c) sensing that all CWA-contaminated surfaces have been properly decontaminated. This can be used as toxic chemical sensors or devices, dielectric indicators, residual life indicators, wearable sensor, decontaminant wipes, and decontaminating sprayable slurry. For use as a chemical sensor or device, the dielectric material could be spray coated on a substrate and used for identification of CWAs. For decontamination of CWAs, the process involves contacting the contaminated surface with the dielectric material. The presence of CWAs and identification is confirmed by changes in IR or other optical spectra and net electric dipole moment. The dielectric material could possibly be reused by first removing the bound CWAs and depolarizing the material. Thereafter, the dielectric material can be re-applied to ascertain the presence of residual CWAs or used in a new contaminated area; thus, extending the life of the dielectric material for recyclable purposes.

Without further description, it is believed that one of ordinary skill in the art can, using the preceding description and the following illustrative examples, make and utilize the articles of the present invention and practice the claimed methods. The following examples are given to illustrate the present invention. It should be understood that the invention is not to be limited to the specific conditions or details described in the examples.

EXAMPLE 2

Methods $BaTiO_3$ was synthesized using the conventional solid-state method by grinding $BaCO_3$ and $TiO_2$ (purchased from Fisher Scientific) for 30 min using an agate mortar and pestle. The resulted mixture was then calcined at 1100° C. for 16 h in air. $BaZrO_3$ and $BaTi_{0.9}Zr_{0.1}O_3$ were also similarly synthesized. For $BaZrO_3$, the reagents were $BaCO_3$ and $ZrO_2$; for $BaTi_{0.9}Zr_{0.1}O_3$, the reagents were $BaCO_3$, $TiO_2$, and $ZrO_2$.

Powder X-ray diffraction ("XRD") patterns were collected using a Rigaku Miniflex 600 X-ray diffractometer, which utilizes a 40 kV, 15 mA, and Cu $K\alpha_1$ radiation ($\lambda$=1.5406 Å) with D/tex high speed silicon strip detector. The scans were taken in 2θ range of 10 to 90° with a step size of 0.01° 2θ, and the count time was 2.0 s/step. Rietveld refinements were performed on X-ray diffraction patterns to confirm phase purity, and refinement results are shown in Table 2 for $BaTiO_3$.

TABLE 2

Lattice parameters, atomic positions, and quality of fit resulting from Rietveld refinement of X-ray powder diffraction data

| Structural Parameters | Calcination Temperature: 1100° C. |
| --- | --- |
| crystallite size (nm) | 28 |
| space group | P4mm |
| a (Å) | 3.99618(5) |
| c (Å) | 4.02972(6) |
| V (Å)$^3$ | 64.352(2) |
| Ba (0, 0, z) | |
| z | −0.004(6) |
| Ti (½, ½, z) | |
| z | 0.488(5) |
| O1 (½, ½, z) | |
| z | −0.11(2) |
| O2 (½, 0, z) | |
| z | 0.560(6) |
| Rwp | 0.0720 |
| Rp | 0.0516 |
| $X^2$ | 13.74 |

Figure 12:
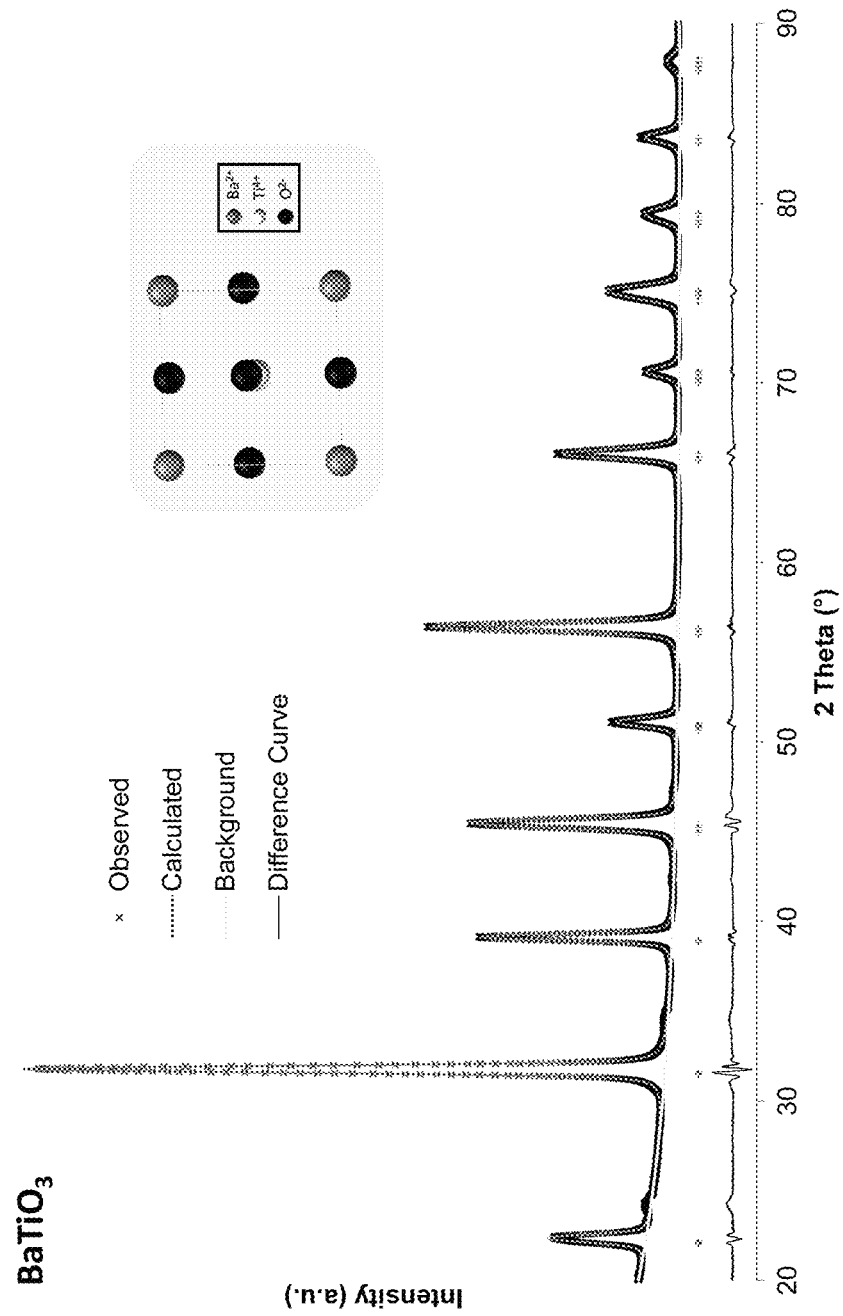
FIG. 12 depicts an X-ray diffraction pattern for $BaTiO_3$ showing the Rietveld refinement using the space group P4mm. The observed pattern, calculated pattern, background curve, difference curve, and allowed Bragg positions are shown as black crosses, grey solid line, light grey solid line, black solid line, and grey crosses, respectively. The structural arrangement of the atoms is shown above the XRD pattern. The black, grey, and white spheres are oxygen, barium, and titanium, respectively.
Figure 13:
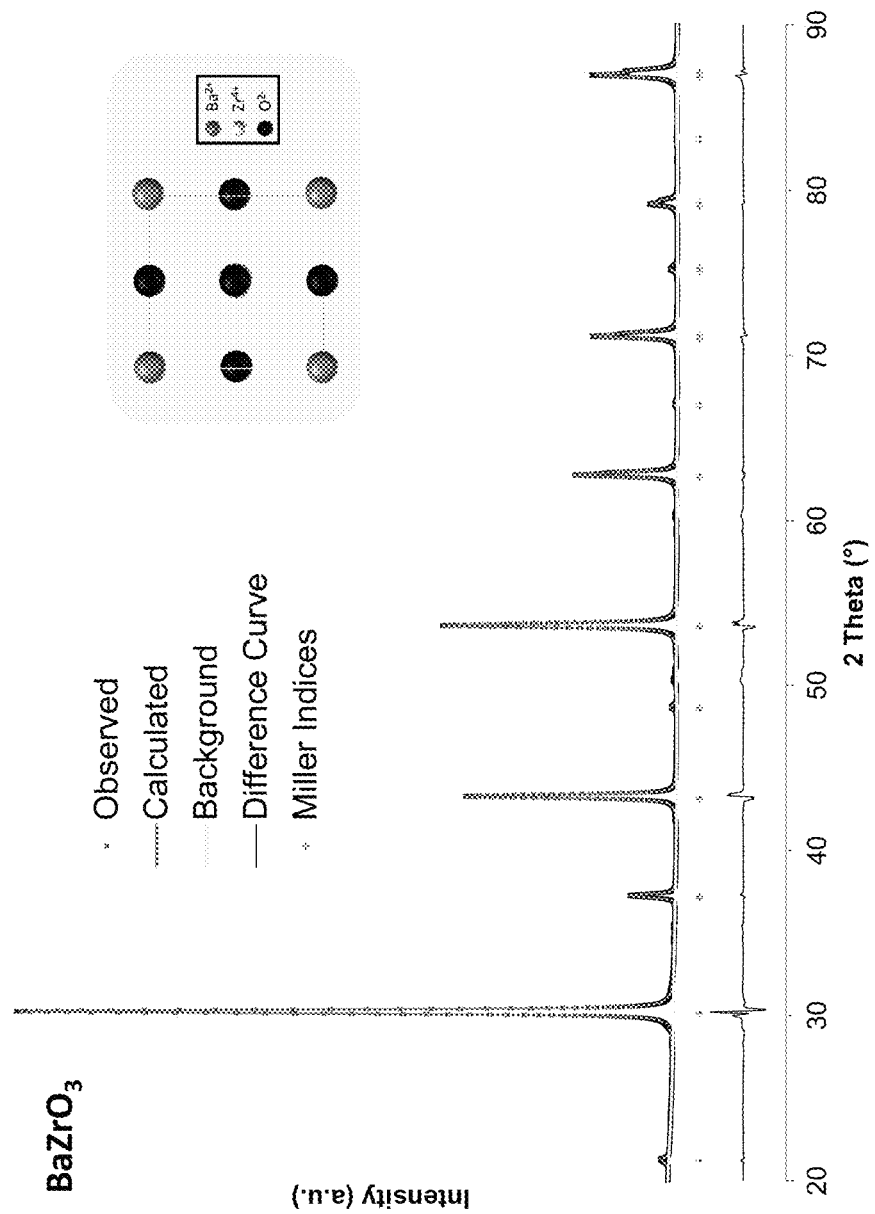
FIG. 13 depicts an X-ray diffraction pattern for $BaZrO_3$ showing the Rietveld refinement using the space group Pm-3m. The observed pattern, calculated pattern, background curve, difference curve, and allowed Bragg positions are shown as black crosses, grey solid line, light grey solid line, black solid line, and grey crosses, respectively. The structural arrangement of the atoms is shown above the XRD pattern. The black, grey, and white spheres are oxygen, barium, and zirconium, respectively.
Figure 14:
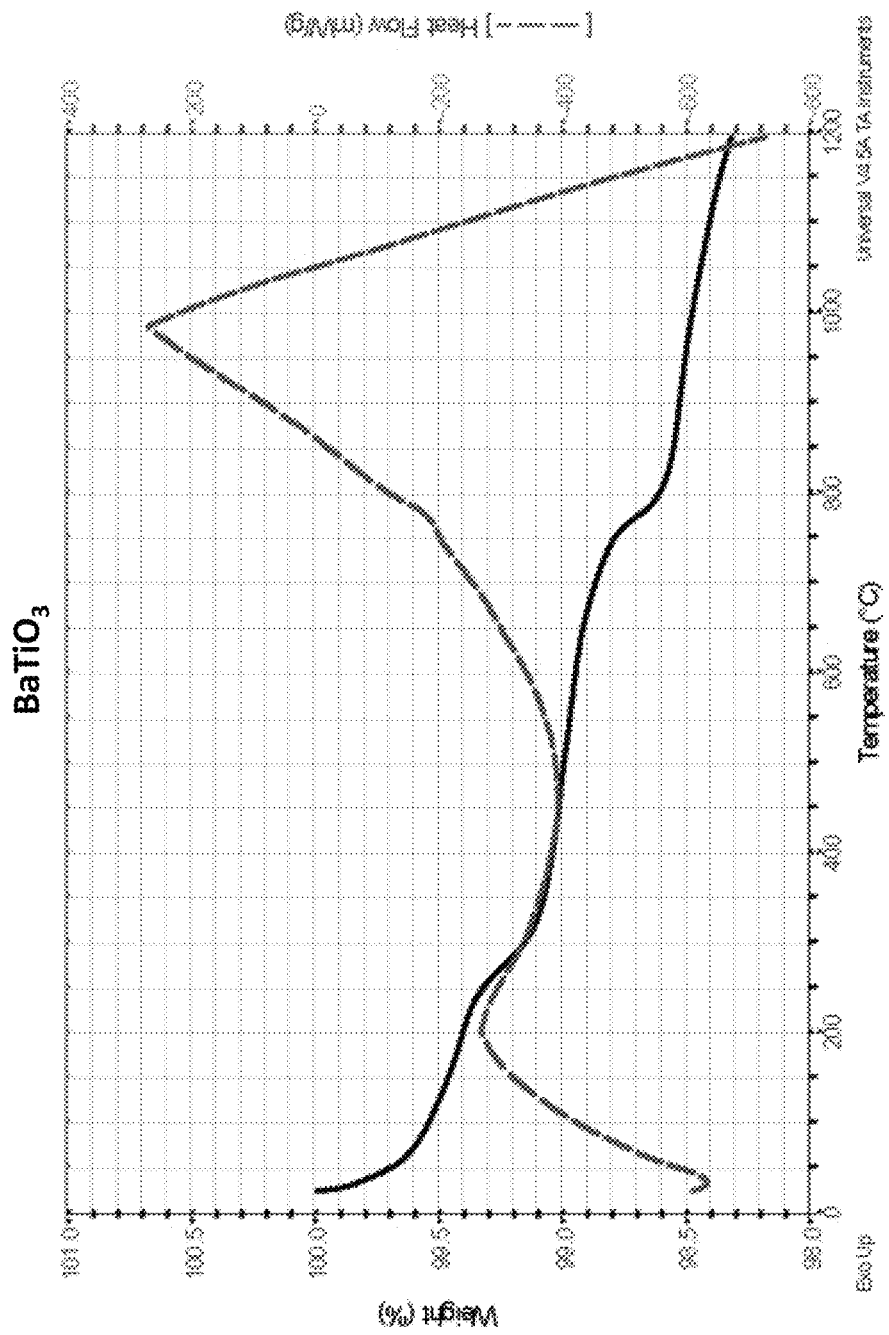
FIG. 14 depicts a thermal gravimetric analysis of $BaTiO_3$. The solid line and dashed line correspond to % weight loss and heat flow, respectively, as a function of temperature.
Figure 15:
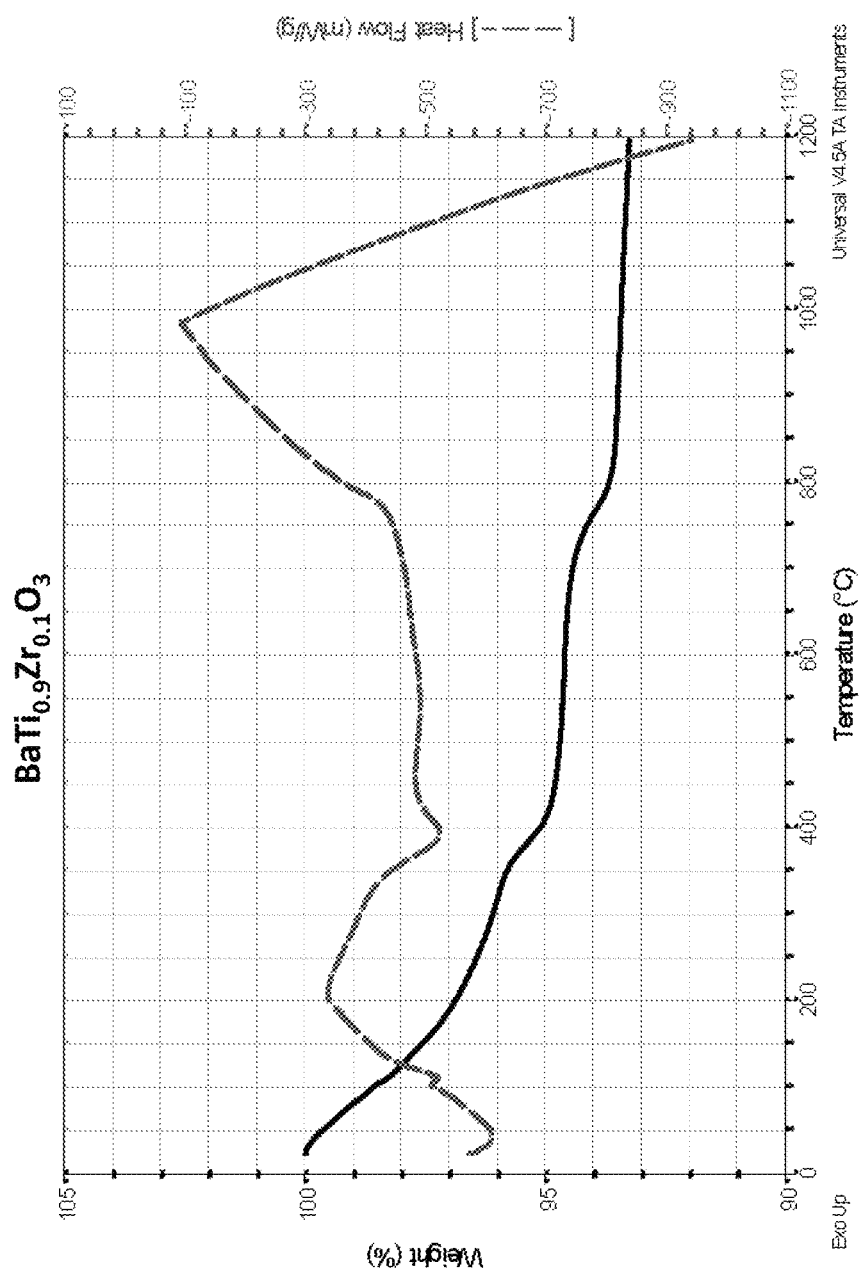
FIG. 15 depicts a thermal gravimetric analysis of $BaTi_0Ti_{0.9}Zr_{0.1}O_3$. The solid line and dashed line correspond to % weight loss and heat flow, respectively, as a function of temperature.

Thermal gravimetric analysis ("TGA") of $BaTiO_3$ was conducted to determine its decomposition, and TGA results were collected using a TA Instruments TGA Q500 instrument and a ramp rate of 2° C/min in air. FIGS. 12 and 14 show the XRD pattern and TGA results, respectively, for $BaTiO_3$; and FIGS. 13 and 15 show the XRD pattern and TGA results, respectively, for $BaTi_{0.9}Zr_{0.1}O_3$.

Impedance measurements were collected using a Solartron Analytical 1260 impedance analyzer equipped with a 1296 dielectric interface. AC impedance measurements were collected on bulk pellets over a frequency range of $10^{-2}$ to $10^6$ Hz and an applied voltage of 100 mV. Measurements were repeated three times and then averaged.

DRIFTS was conducted using a Harrick cell accessory mounted on the internal compartment of a Thermo Nicolet 6700 FTIR spectrometer. Briefly, both the $BaTiO_3$ and DMCP-exposed $BaTiO_3$ samples were loosely packed into a 3 mm diameter ceramic cup and transferred to the Harrick cell. Once inside the cell, each sample was purged for 20 minutes in dry air, and the FTIR spectra were collected at a resolution of 2 cm$^{-1}$ and with an average of 256 interferograms per spectrum. The background spectrum was collected using KBr powder with the same parameters and experimental conditions as the samples.

$^{31}$P MAS NMR spectra were collected on 50 mg samples exposed to 10 wt. % of sarin and DMCP at ambient temperature using a Varian INOVA 400 NB NMR spectrometer equipped with a Doty Scientific 7 mm standard speed MAS NMR probe for monitoring the reaction and identifying the products. Samples were spun at 1.5-5 kHz with scan times of 8 min employing 90° pulse width (11μs), gain of 60, pulse width of 6.5μs, and total power of 60 W. Total acquisition time for each measurement was 813 min.

Using a Jasco V-750 spectrophotometer equipped with the 60 mm integrating sphere, we collected the ultra-violet visible (UV-Vis) spectra on the unexposed and exposed $BaTiO_3$ and $BaTi_{0.9}Zr_{0.1}O_3$.

Results

Figure 1:
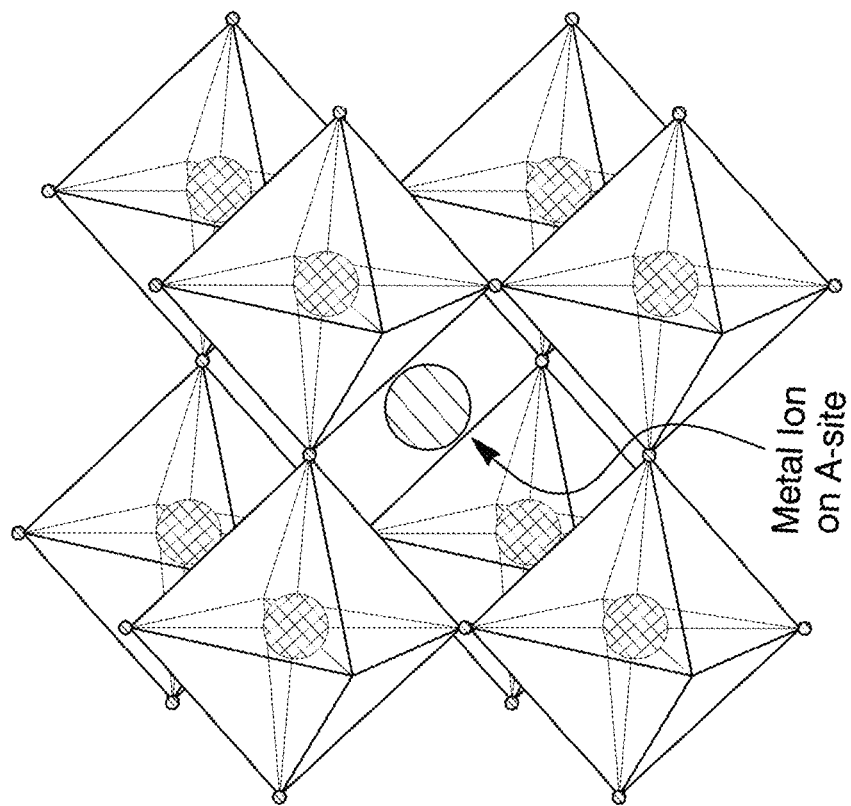
FIG. 1 is a drawing depicting a simple cubic perovskite structure showing (left) the octahedrally coordinated B-site cation surrounded by the X-site anions and (right) showing the A-site cation at the center of the corner sharing $BX_6$ octahedra.
Figure 1:
Figure 1:
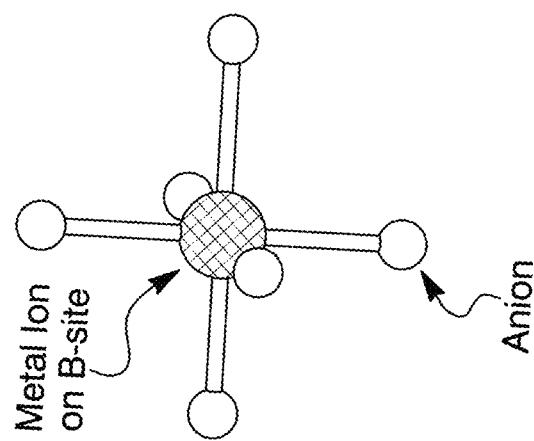
Figure 2B:
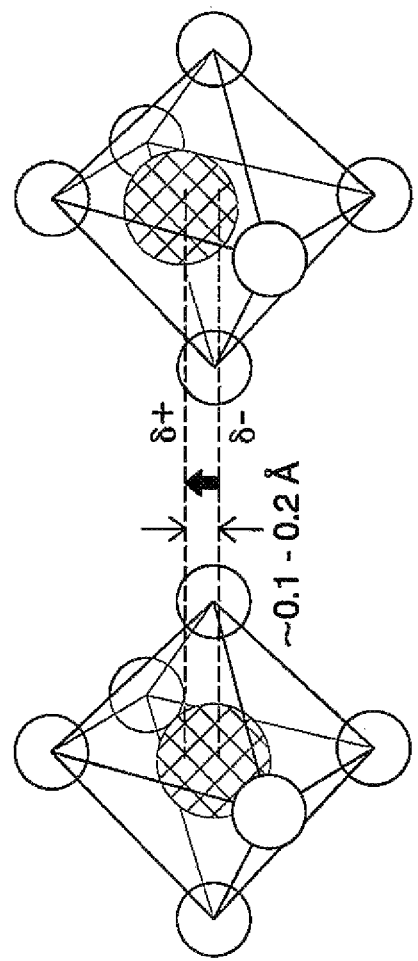
FIGS. 2A and 2B depict the B-site cation (sphere in center) shifts out of the center of an octahedron, to produce a net dipole moment. White spheres at edge center sites and spheres at corner sites of the cube are the anions and B-site cations, respectively. The figures show the crystal structure of (FIG. 2A) cubic $BaTiO_3$ and (FIG. 2B) shift in Ti atoms from out of the center of the polyhedron, leading to tetragonal $BaTiO_3$.
Figure 2A:
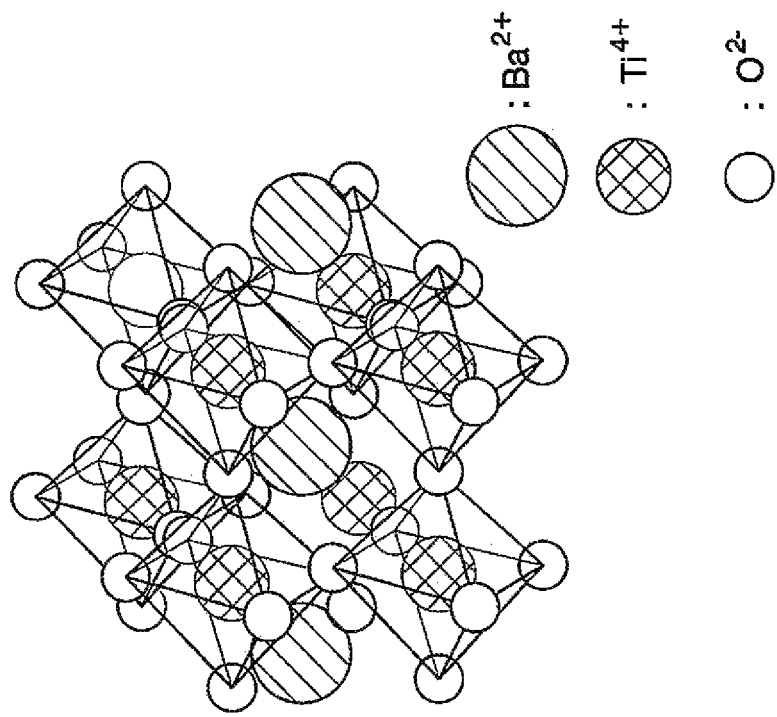
Figure 3:
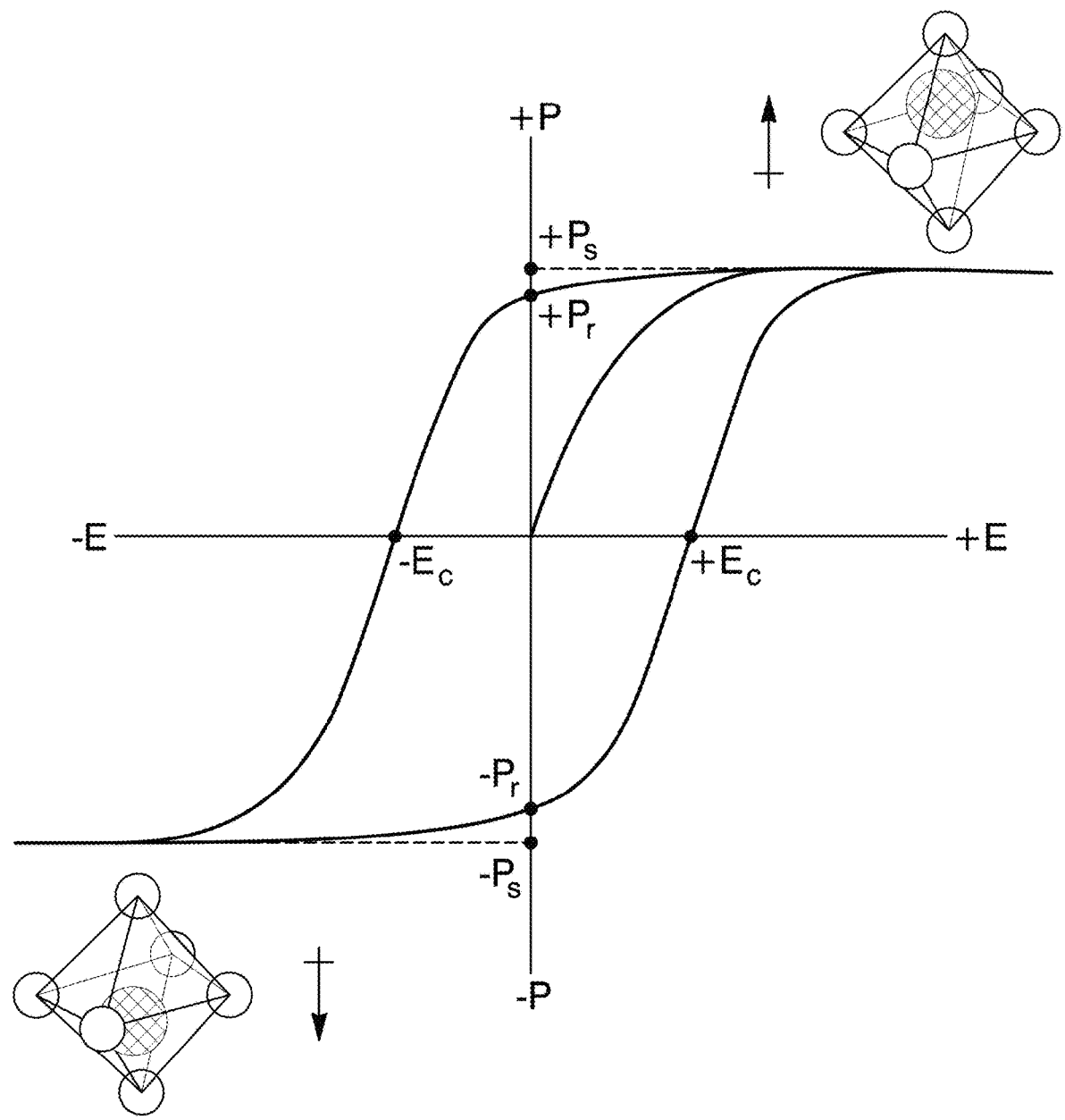
FIG. 3 depicts a hysteresis loop generated by an electric field. The $P_S$ is the saturation of the polarization, the $P_r$ is the remnant polarization, and the $E_c$ is the coercivity strength. The octahedra show the shift of the B-site cations as the electric field is switched, causing the material to polarize.
Figure 18:
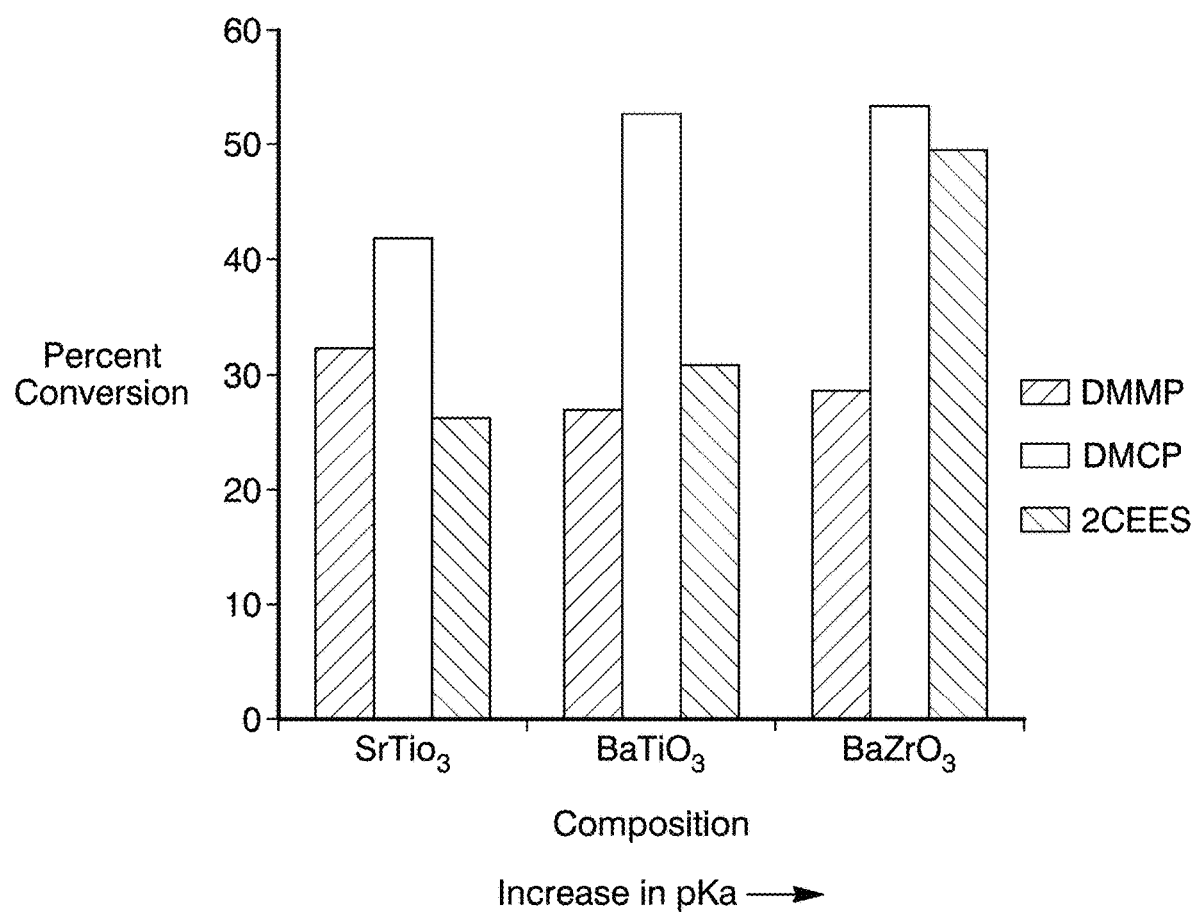
FIG. 18 depicts a conversion of DMMP, DMCO, and 2CEES when these chemicals were absorbed by SrTiO3, $BaTiO_3$, and $BaZrO_3$.

BaTiO$_3$ ("BTO") is one of the desirable perovskites owing to its structural polarization, shifting the Ti atoms from out of the polyhedra center (FIG. 2) as an electric field is applied. A test was conducted to measure removal by BTO, BaZrO$_3$, and control SrTiO$_3$ of analytes dimethyl chlorophosphate (DMCP, an often-used structural analog for sarin), 2-chloroethyl ethyl sulfide (2-CEES, an often-used structural analog for sulfur mustard), and sarin. The ferroelectric was exposed with 10 weight % each of the analytes. Impedance measurements showed BTO and BaZrO$_3$ are sensitive to detect changes from exposure. The results are shown in FIG. 18.

Figure 8A:
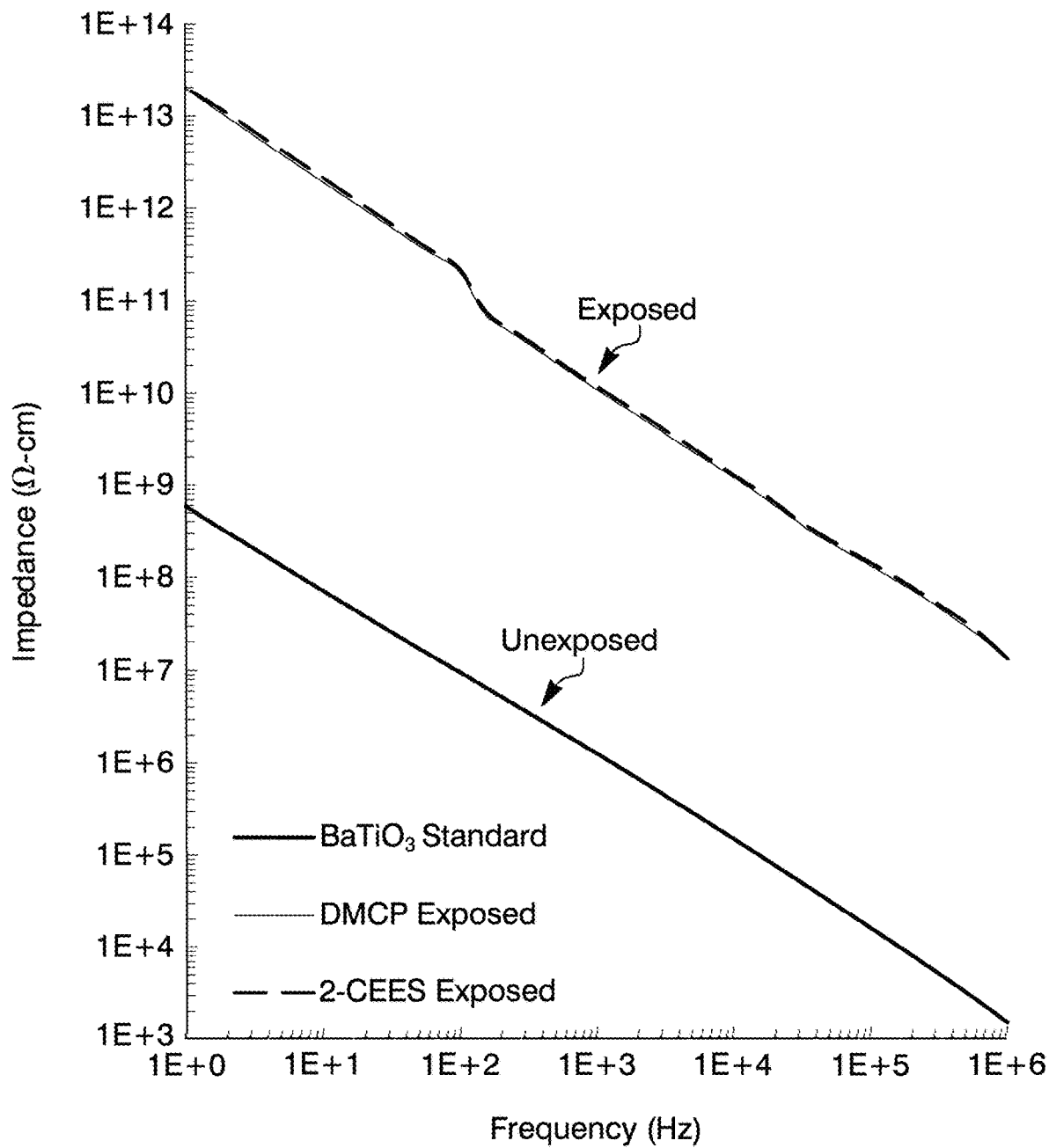
FIGS. 8A and 8B depict respectively a frequency dependent impedance magnitude (FIG. 8A) and dielectric constant (FIG. 8B), respectively, of unexposed (black line) and CWA exposed (grey lines) $BaTiO_3$.
Figure 8B:
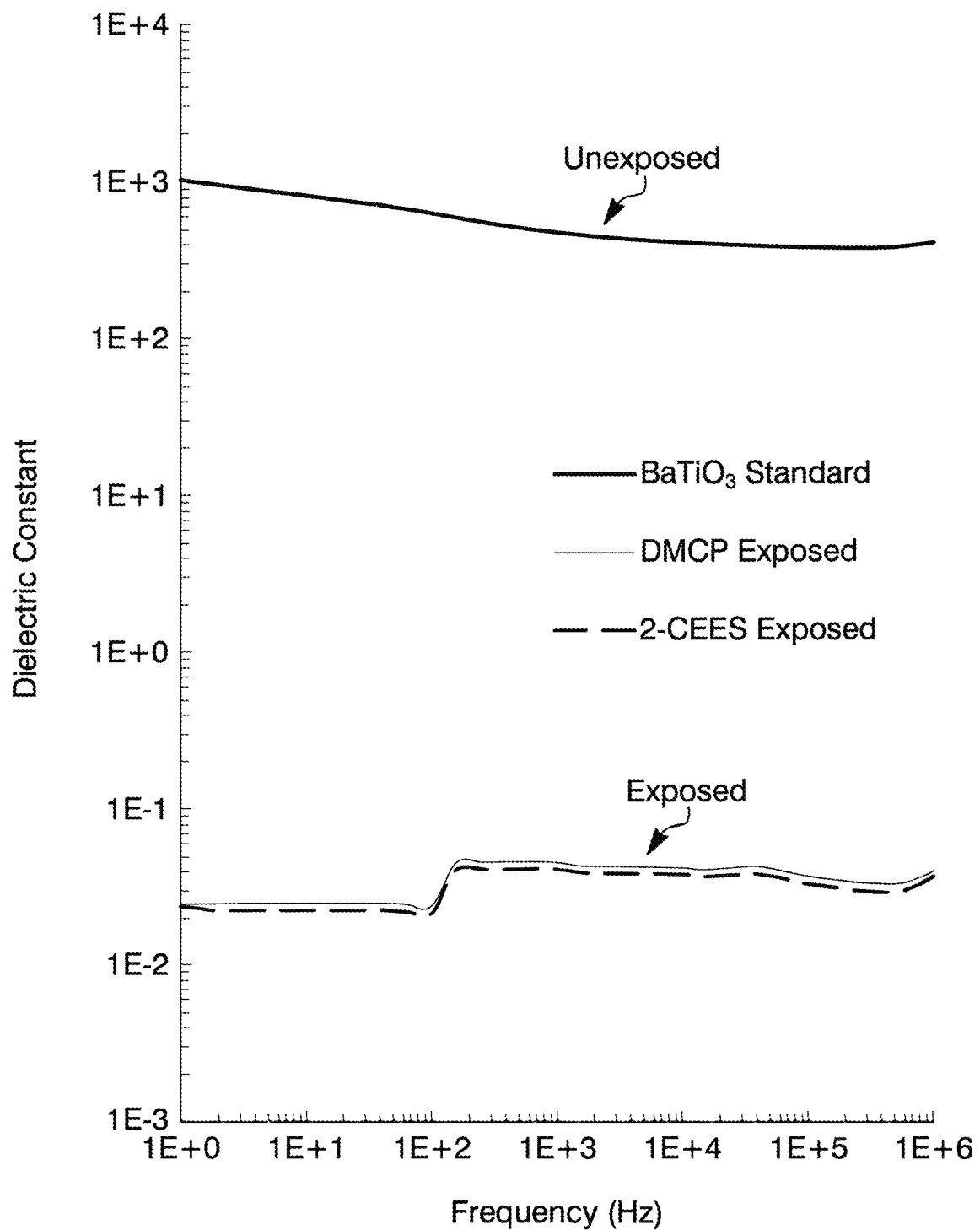
Figure 9A:
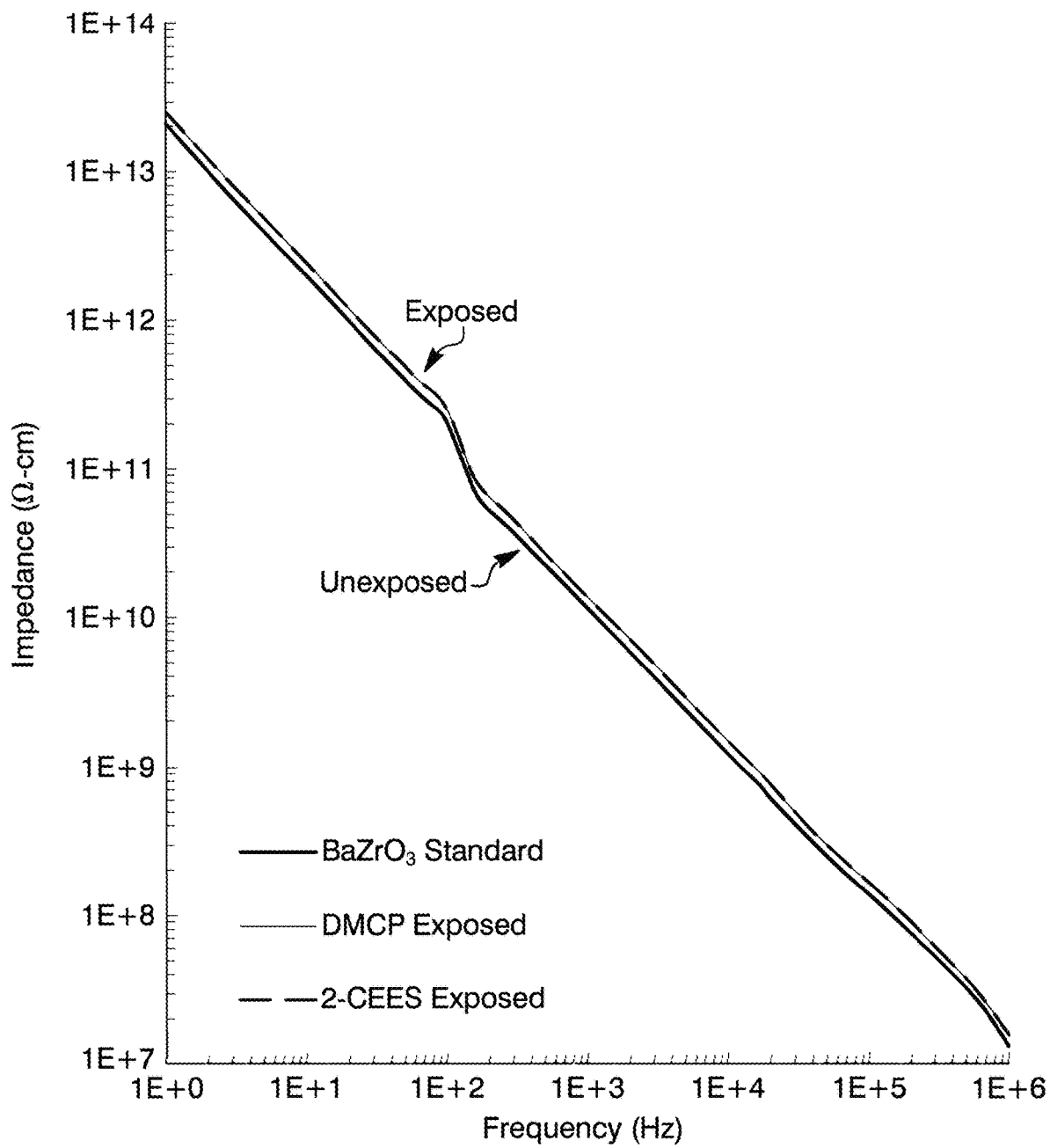
FIGS. 9A and 9B depict respectively a frequency dependent impedance magnitude (FIG. 9A) and dielectric constant (FIG. 9B), respectively, of unexposed (black line) and CWA exposed (grey lines) $BaZrO_3$.
Figure 9B:
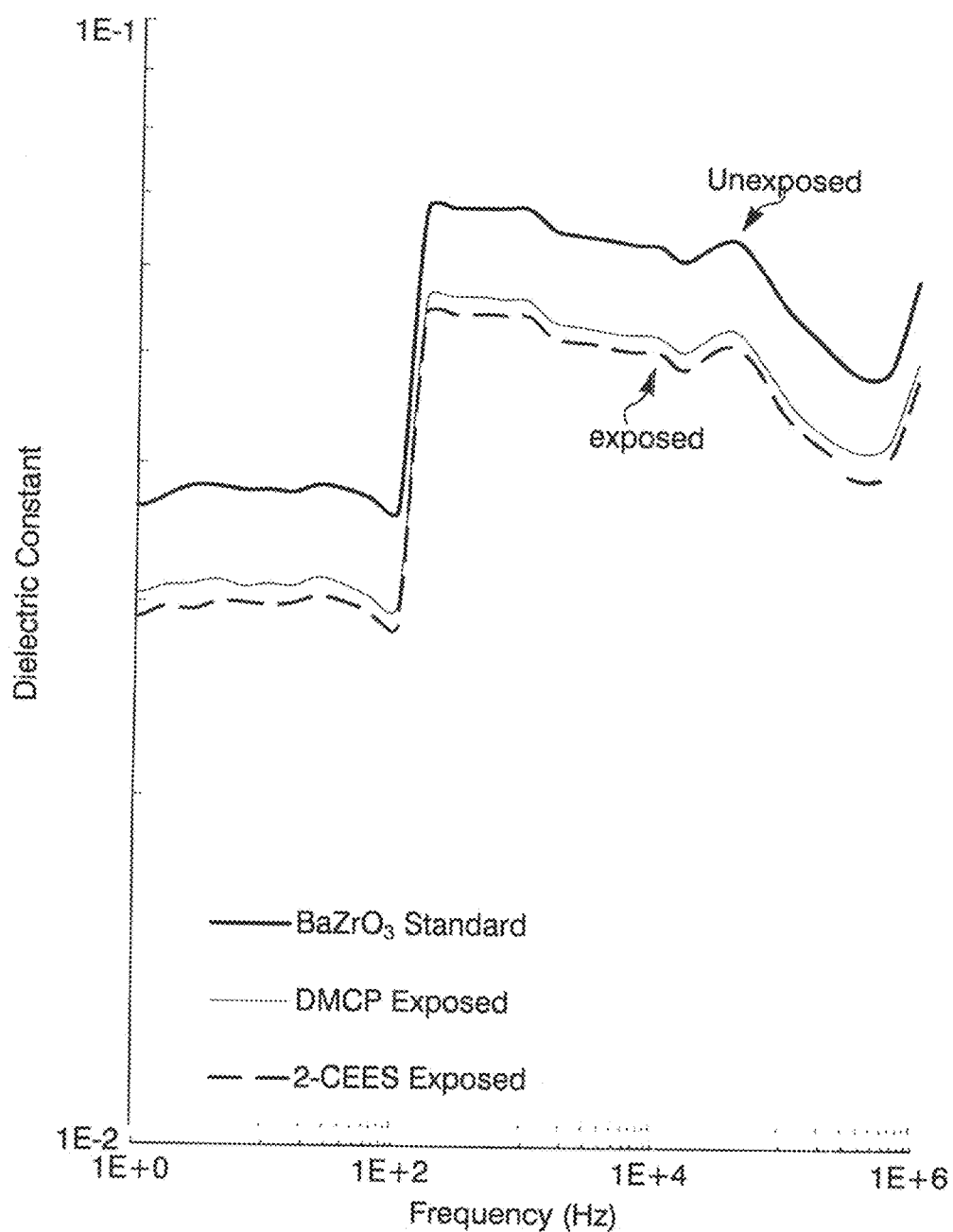

The magnitude 171 and dielectric constant of the impedance measured as a function of frequency with an applied voltage of 100 mV is shown in FIGS. 8A and 8B, respectively, for BaTiO$_3$, and in FIGS. 9A and 9B, respectively, for BaZrO$_3$. There is a significant increase in impedance across the entire frequency range from exposure, increasing by at least four orders of magnitude. These results are plotted in log scale, which allows one to capture the impact in the impedance changes. These results can be used to begin establishing a database of fingerprint responses for the chemical interactions.

Figure 10A:
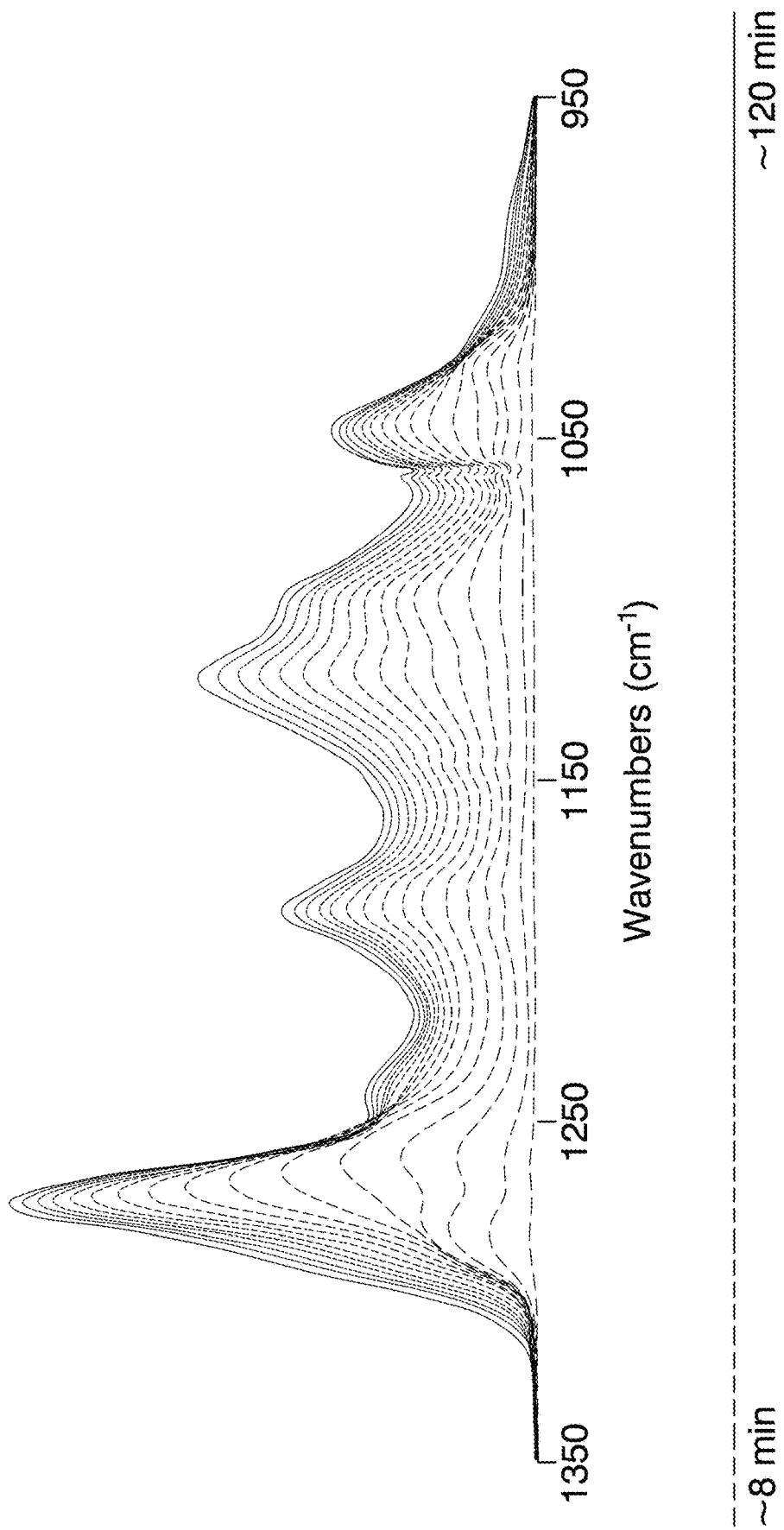
FIGS. 10A and 10B depict respectively a diffuse reflectance infrared Fourier transform spectra (DRIFTS) of $BaTiO_3$ vapor exposed to DMCP (FIG. 10A) and 2-CEES (FIG. 10B) over the period of 2 hours. The wavenumbers regime is shown from 1350 to 950 $cm^{-1}$.
Figure 10B:
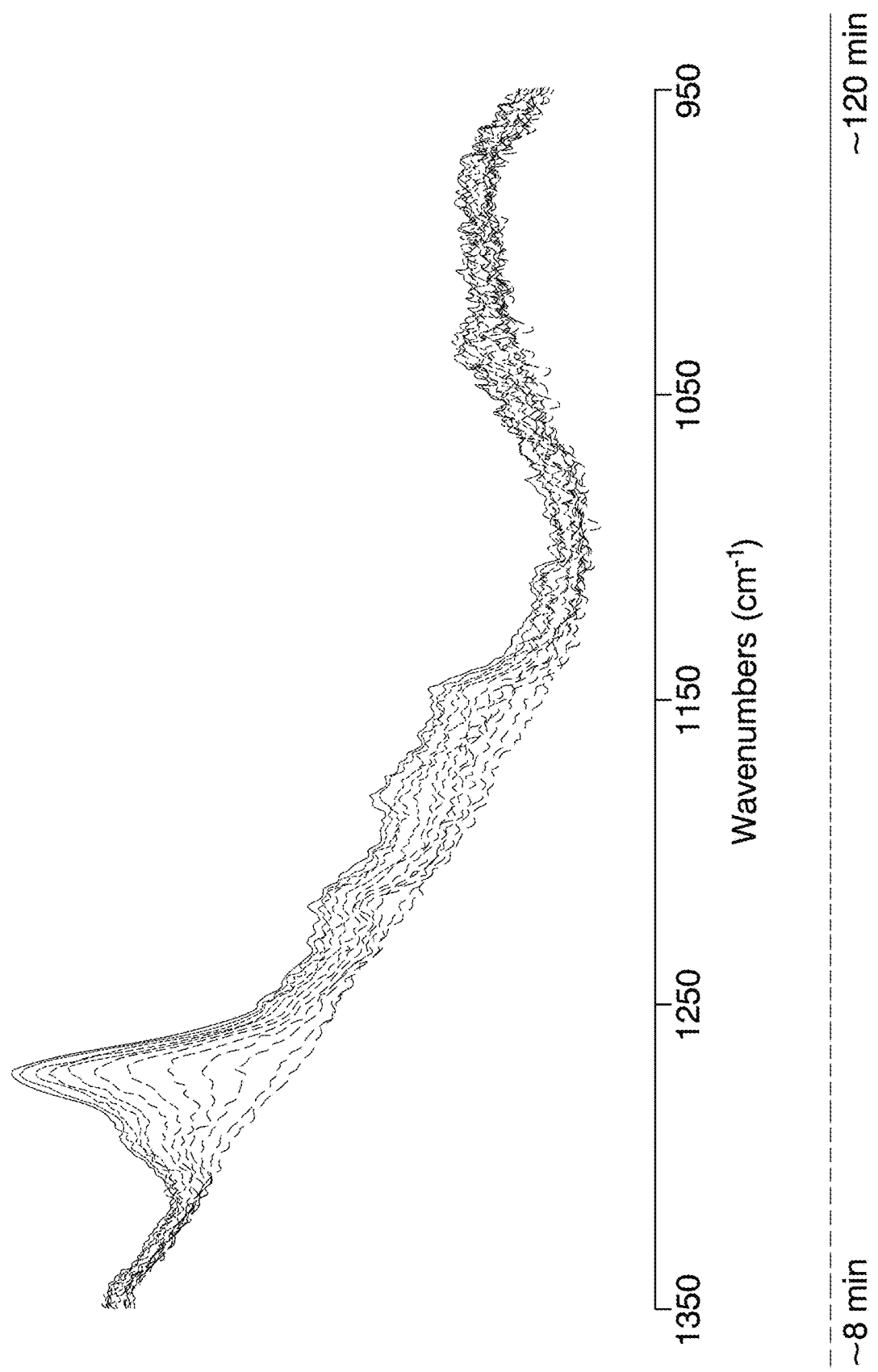
Figure 11A:
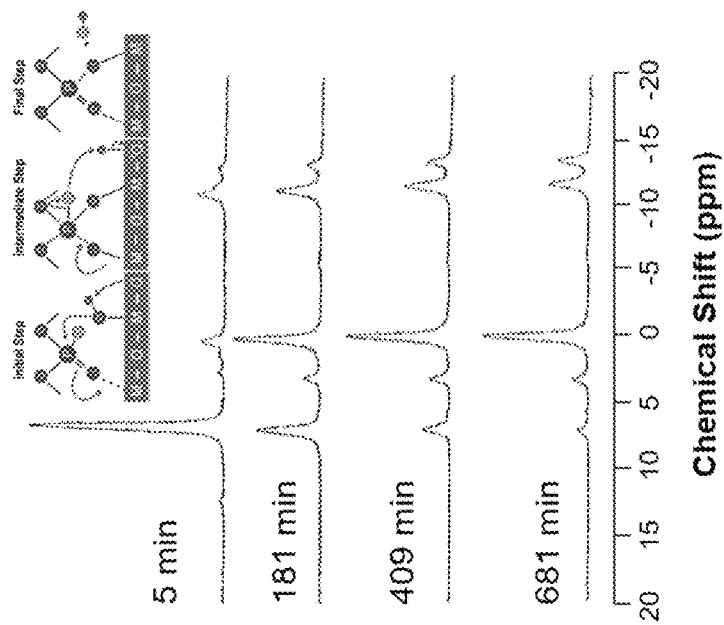
FIGS. 11A and 11B depict respectively the magic angle spinning nuclear magnetic resonance plots of $BaTiO_3$ exposed to DMCP (FIG. 11A) and sarin (FIG. 11B). The mechanism of the chemical reaction with the respective analyte is shown above each plot.
Figure 11B:
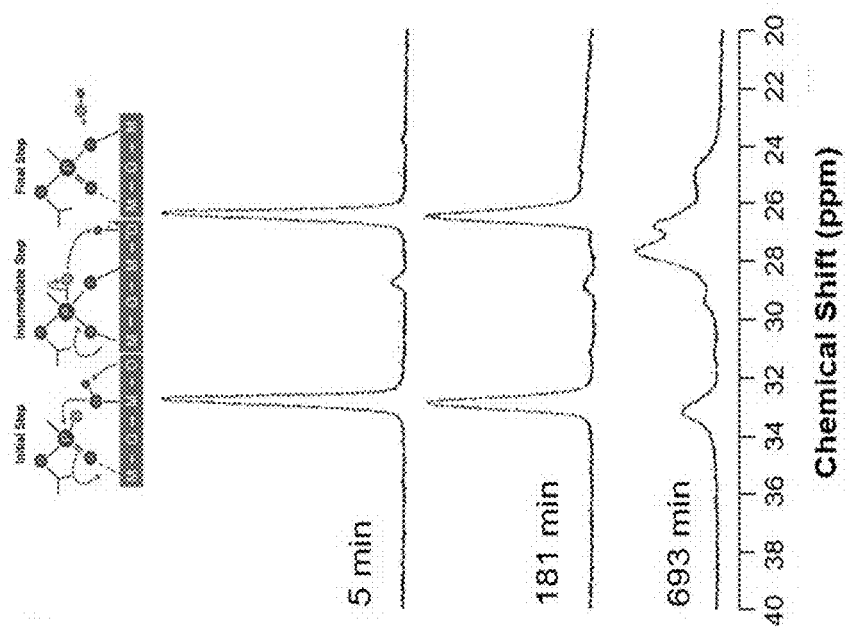
Figure 16A:
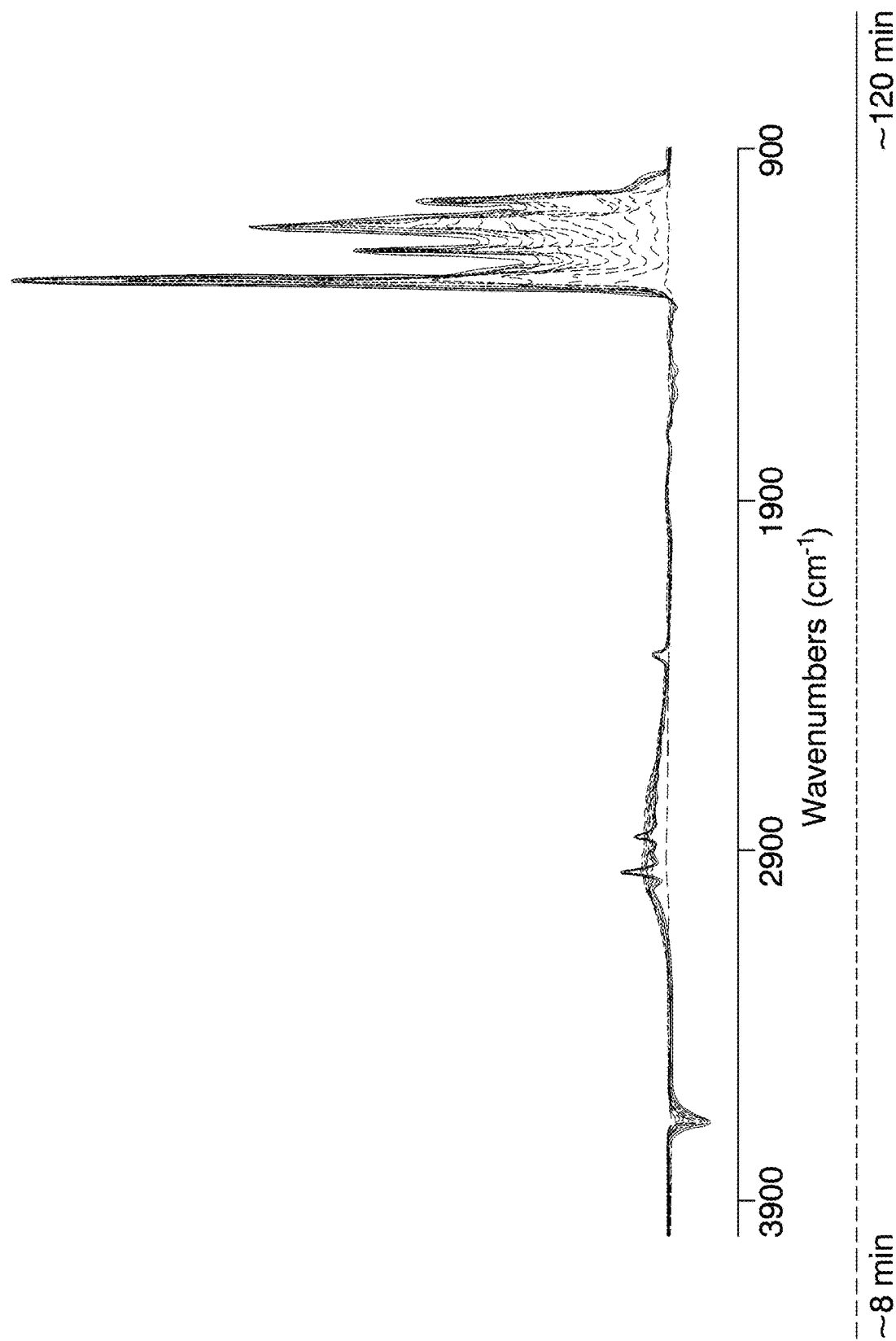
FIGS. 16A and 16B respectively depict diffuse reflectance infrared Fourier transform spectra (DRIFTS) of $BaTiO_3$ vapor exposed to DMCP (FIG. 16A) and 2-GEES (FIG. 16B) over the period of 2 hours. The wavenumbers regime is shown from 4000 to 900 $cm^{-1}$.
Figure 16B:
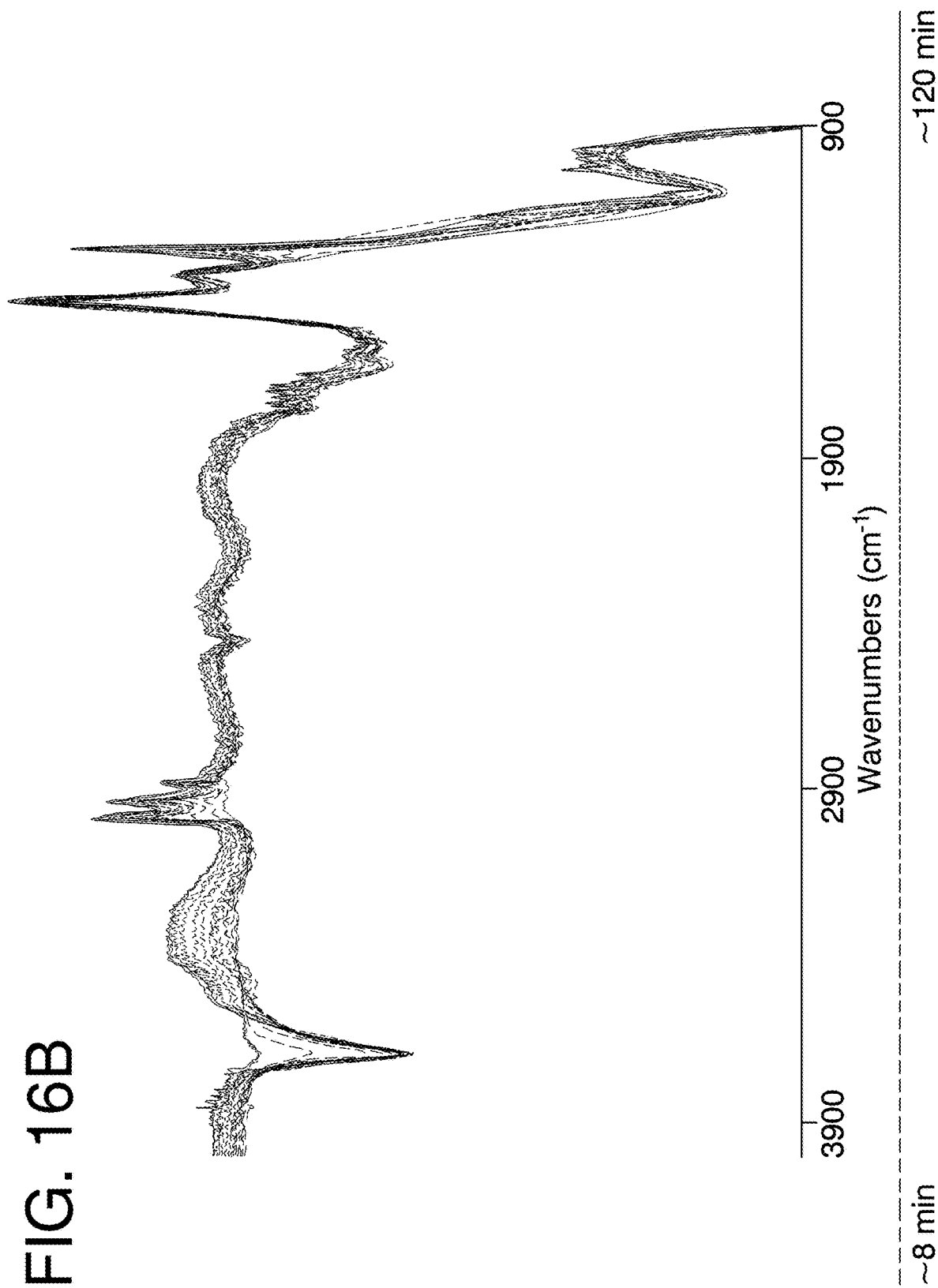

To elucidate these results, the diffuse reflectance infrared Fourier transform spectroscopy (DRIFTS) and magic angle spinning nuclear magnetic resonance (MAS NMR) on exposed BTO were collected. DRIFTS (FIGS. 10A, 10B, 16A and 16B) shows the 10 wt. % CWA structural analogs exposed BTO over 2 h. Several distinct changes of the structure are observed after CWA exposure. From 2934 to 2860 cm$^{-1}$, broad IR peaks are present, corresponding to the v(-CH$_2$), v(CH$_3$O), and v(CH$_3$) stretches, which are shown in FIGS. 16a and 16b. More importantly, we observed the v(P=O) as well as the v(P—O) peaks at 1274 cm$^{-1}$ and 1120 cm$^{-1}$, respectively, indicating the molecular dissociation of DMCP (FIG. 10A). In addition, BTO showed the molecular breakdown of 2-CEES as indicated by the v(M—O—CH$_2$) peak at 1145 cm$^{-1}$ (see FIG. 10B). IR shifts corresponding to interactions from the CWAs with BTO are observed, indicating chemisorption. To interpret the mechanism for removing these CWA structural analogs as well as confirm molecular dissociation of sarin, MAS NMR data was collected (FIGS. 11A and 11B). FIG. 11A shows the peak at about 0 ppm increase due to BTO binding to DMCP, and in FIG. 11B, the peak at about 27.5 ppm increases over time, showing the formation of isopropyl methyiphosphonic acid (by-product of sarin). These combined results confirm the charge transfer of the nucleophile attacking the CWAs, exploiting this oxide as a promising candidate for the removal of CWAs. Thus, the combination of a ferroelectric and oxide may provide the enhanced capability for detection.

Although certain preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

The invention claimed is:

1. A sensor for the absorption and detection of a toxic chemical, comprising:
   a substrate;
   at least one sensing layer coated onto at least one surface of said substrate, wherein said at least one sensing layer comprises BaTi$_{1-x}$Zr$_x$O$_3$ wherein 0<x<1;
   a pair of electrodes coupled to said at least one sensing layer and a power source to create a circuit through said at least one sensing layer; and
   wherein a change in impedance is measured in said circuit to detect the absorption of the toxic chemical because said at least one sensing layer changes impedance in said circuit upon exposure to the toxic chemical; and
   wherein the toxic chemical is a chemical warfare agent or a narcotic.

2. The sensor of claim 1, wherein said substrate is a textile material, crystalline or amorphous structural support, a polymer, a dielectric, paper, a film, a fabric, or a foam.

3. A method for absorbing and detecting a toxic chemical in a sample, comprising the steps of:
   contacting the sensor of claim 1 with said sample; and
   measuring a change in impedance in the circuit of said sensor to indicate a presence of said toxic chemical.

4. The method of claim 3, wherein when measuring the change in impedance, an increase in impedance of at least one-fold indicates the presence of said toxic chemical.

5. The method of claim 3, wherein the toxic chemical is a chemical warfare agent, an industrial chemical, or a narcotic.

* * * * *